US011839642B2

(12) United States Patent
Mao et al.

(10) Patent No.: US 11,839,642 B2
(45) Date of Patent: Dec. 12, 2023

(54) ANTI-ANGIOGENIN PEPTIDES, COMPOSITIONS, AND METHODS OF USE

(71) Applicant: The Board of Regents of the University of Oklahoma, Norman, OK (US)

(72) Inventors: Chuanbin Mao, Norman, OK (US); Yan Li, Norman, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 846 days.

(21) Appl. No.: 16/623,684

(22) PCT Filed: Apr. 9, 2019

(86) PCT No.: PCT/US2019/026540
§ 371 (c)(1),
(2) Date: Dec. 17, 2019

(87) PCT Pub. No.: WO2019/199790
PCT Pub. Date: Oct. 17, 2019

(65) Prior Publication Data
US 2020/0384066 A1    Dec. 10, 2020

Related U.S. Application Data

(60) Provisional application No. 62/655,357, filed on Apr. 10, 2018.

(51) Int. Cl.
*A61K 38/10* (2006.01)
*A61K 47/69* (2017.01)
(Continued)

(52) U.S. Cl.
CPC .............. *A61K 38/10* (2013.01); *A61K 35/76* (2013.01); *A61K 47/6901* (2017.08);
(Continued)

(58) Field of Classification Search
None
See application file for complete search history.

(56) References Cited

U.S. PATENT DOCUMENTS

| 8,653,034 B2 | 2/2014 | Thorpe et al. |
| 9,562,083 B2* | 2/2017 | Yeaman ............. A61K 47/6415 |

(Continued)

FOREIGN PATENT DOCUMENTS

| WO | 2005054273 A2 | 6/2005 |
| WO | 2007146968 A2 | 12/2007 |
| WO | 2018045155 A1 | 3/2018 |

OTHER PUBLICATIONS

Li et al. (International Journal of Nanomedicine. 2016; 11: 93-105).*
(Continued)

*Primary Examiner* — Shanon A. Foley
(74) *Attorney, Agent, or Firm* — Hall Estill Law Firm; Michael H. Smith

(57) ABSTRACT

Carrier compositions, including human-safe phages, equipped with one or more angiogenin-binding peptides, and optionally with tumor-homing peptides for use in anti-tumor therapies, are described. The angiogenin-binding peptides bind to and inactivate angiogenin molecules thereby blocking their angiogenic activity thus inhibiting angiogenesis in the tissue in which the compositions are localized.

20 Claims, 9 Drawing Sheets

Specification includes a Sequence Listing.

(51) Int. Cl.
| | |
|---|---|
| A61P 35/00 | (2006.01) |
| C12N 7/00 | (2006.01) |
| A61K 35/76 | (2015.01) |
| C07K 14/47 | (2006.01) |
| C07K 17/00 | (2006.01) |
| C12Q 1/6883 | (2018.01) |

(52) U.S. Cl.
CPC .......... *A61P 35/00* (2018.01); *C07K 14/4703* (2013.01); *C07K 17/00* (2013.01); *C12N 7/00* (2013.01); *C12Q 1/6883* (2013.01); *C12N 2795/14132* (2013.01); *C12N 2795/14171* (2013.01)

(56) References Cited

U.S. PATENT DOCUMENTS

| | | | | |
|---|---|---|---|---|
| 9,657,077 | B2* | 5/2017 | Li | G01N 33/57423 |
| 10,179,801 | B2* | 1/2019 | Ruoslahti | C07K 7/08 |
| 2005/0112134 | A1 | 5/2005 | Graddis et al. | |
| 2014/0325702 | A1 | 10/2014 | Boukharov et al. | |
| 2020/0384066 | A1* | 12/2020 | Mao | C12N 7/00 |

OTHER PUBLICATIONS

Yang et al. (Chemical Communications. Feb. 2018; 54 (13): 1631-1634).*

Li et al. (Advanced Materials. 2020; 32 (29): 2001260).*

Gho, Y.S., et al.; "Development of Antiangiogenin Peptide Using a Phage-Displayed Peptide Library"; Cancer Research 57 (1997) 3733-3740.

Frenkel, D., et al.; "Filamentous phage as vector-mediated antibody delivery to the brain"; PNAS 99:8 (2002) 5675-5679.

Krag, D.N., et al.; "Selection of Tumor-binding Ligands in Cancer Patients with Phage Display Libraries"; Cancer Res 66:15 (2006) 7724-8925.

Yoshioka, N., et al.; "A therapeutic target for prostate cancer based on angiogenin-stimulated angiogenesis and cancer cell proliferation"; PNAS 103:39 (2006) 14519-14524.

Butler, G., et al.; "Evolution of pathogenicity and sexual reproduction in eight Candida genomes"; Nature 459:7247 (2009) 657-662.

Staquicini, F.I., et al.; "Vascular ligand-receptor mapping by direct combinatorial selection in cancer patients"; PNAS 108:46 (2011) 18637-18642.

Ghosh, D., et al.; "M13-templated magnetic nanoparticles for targeted in vivo imaging of prostate cancer"; Nat Nantechnol. 7:10 (2012) 677-682.

Wang, J., et al.; "Phage nanofibers induce vascularized osteogenesis in 3D printed bone scaffolds"; Adv Mater. 36:29 (2014) 4962-4966.

Wang, Y., et al.; "Ultrasenstive Rapid Detection of Human Serum Antibody Biomarkers by Biomark-Capturing Viral Nanofibers"; ACS Nano 9:4 (2015) 4475-4483.

Qu, X., et al.; "Guiding nanomaterials to tumors for breast cancer precision medicine: from tumor-targeting small-molecule discovery to targeted nanodrug delivery"; NPG Asia Materials 9 (2017) 7 pages.

Yang, M., et al.; "Virus-Derived Peptides for Clinical Applications"; Chem Rev. 117:15 (2017) 10377-10402.

Yang, M., et al.; "Evolutionary selection of personalized melanoma cell/tissue dual-homing peptides for guiding bionanofibers to malignant tumors"; Chem. Commun. 54 (2018) 1631-1634.

PCT/US2019/026540; "International Search Report and Written Opinion"; International Searching Authority/US; dated Oct. 9, 2019; 14 pages.

* cited by examiner

ANTI-ANGIOGENIN PEPTIDES, COMPOSITIONS, AND METHODS OF USE

CROSS-REFERENCE TO RELATED APPLICATIONS

The present application is a national stage application of a PCT application having International Application No. PCT/US2019/062540, filed Apr. 9, 2019, which claims priority to U.S. Provisional Application having U.S. Ser. No. 62/655,357, filed Apr. 10, 2018, which claims the benefit under 35 U.S.C. 119(e), the disclosure of which is hereby expressly incorporated herein by reference.

GOVERNMENT SUPPORT

This invention was made with government support under Contract Number CA200504 awarded by the National Institutes of Health. The government has certain rights in the invention.

BACKGROUND

Tumor growth requires new blood vessels to deliver oxygen and nutrients and removal of waste products for their survival. Hence, new blood vessel formation (i.e., angiogenesis) could promote tumor growth, immune escape and metastasis to other organs. Angiogenic factors, such as angiogenin, over-expressed and released by the cancer cells (e.g., breast cancer) could open the "angiogenic switch" to drive the new vessel formation, favoring the subsequent tumor growth. It was found that the tumors could not exceed a size of over 2 mm$^3$ or metastasize to other organ in the absence of the angiogenesis. The vessels in the tumors exhibit structures and functions different from those in the normal tissues. The tumor vessels have the disorganized shunts, excessive branching and uneven diameters, leading to acidic and hypoxic tumor micro-environment with high fluid pressure. Such pathological micro-environment will induce angiogenesis and cancer cell proliferation. Moreover, the mosaic tumor vessel walls have transcellular holes, endothelial fenestrae, and a discontinuous or absent basement membrane, resulting in a high vascular permeability. So the primary cancer cells could easily invade and enter blood through the newly formed mosaic vessel walls to advance the metastasis.

The tumor angiogenesis, also known as neovascularization and distinct from the vasculogenesis, involves the generation of new abnormal capillaries by intussusception and sprouting from the preexisting vessels. Angiogenin, a 14 kDa protein, is a most potent angiogenic factor secreted by tumors. The over-expression and secretion of angiogenin is found to accompany the transition from benign to malignant breast carcinoma. Studies indicated that angiogenin induces the endothelial cell proliferation, migration and tube formation by two ways. One is to activate the protein kinase B/Akt to induce the angiogenesis after binding to its receptor (FHL3, Four-and-a-half LIM-only protein 3) of endothelial cells. Another is to process the endocytosis and the nuclear translocation to induce the angiogenesis after it binds to the receptor. Moreover, nuclear angiogenin in the endothelial cells is necessary for angiogenesis induced by other angiogenic factors (e.g., VEGF, FGF). Namely, if angiogenin is blocked, some of the other angiogenic factors will lost their angiogenic functions. As a result, the angiogenin will not be available to function to promote the angiogenesis, which will in turn likely inhibit the tumor angiogenesis. It is interesting that so far, almost no efforts have been made to inhibit tumor growth through scavenging the angiogenin to inhibit the angiogenesis. Therefore, we hypothesize that using a bionanofiber to capture the tumor-derived angiogenin before it enters into the vascular endothelial cell will make the angiogenin unavailable for tumor angiogenesis and thus inhibit tumor growth.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the inventive concepts disclosed herein. The figures are not necessarily to scale and certain features and certain views of the figures may be shown as exaggerated in scale or in schematic in the interest of clarity and conciseness. The patent or application file contains at least one drawing executed in color. Copies of this patent or patent application publication with color drawing(s) will be provided by the Office upon request and payment of the necessary fee.

DETAILED DESCRIPTION

Figure 1:
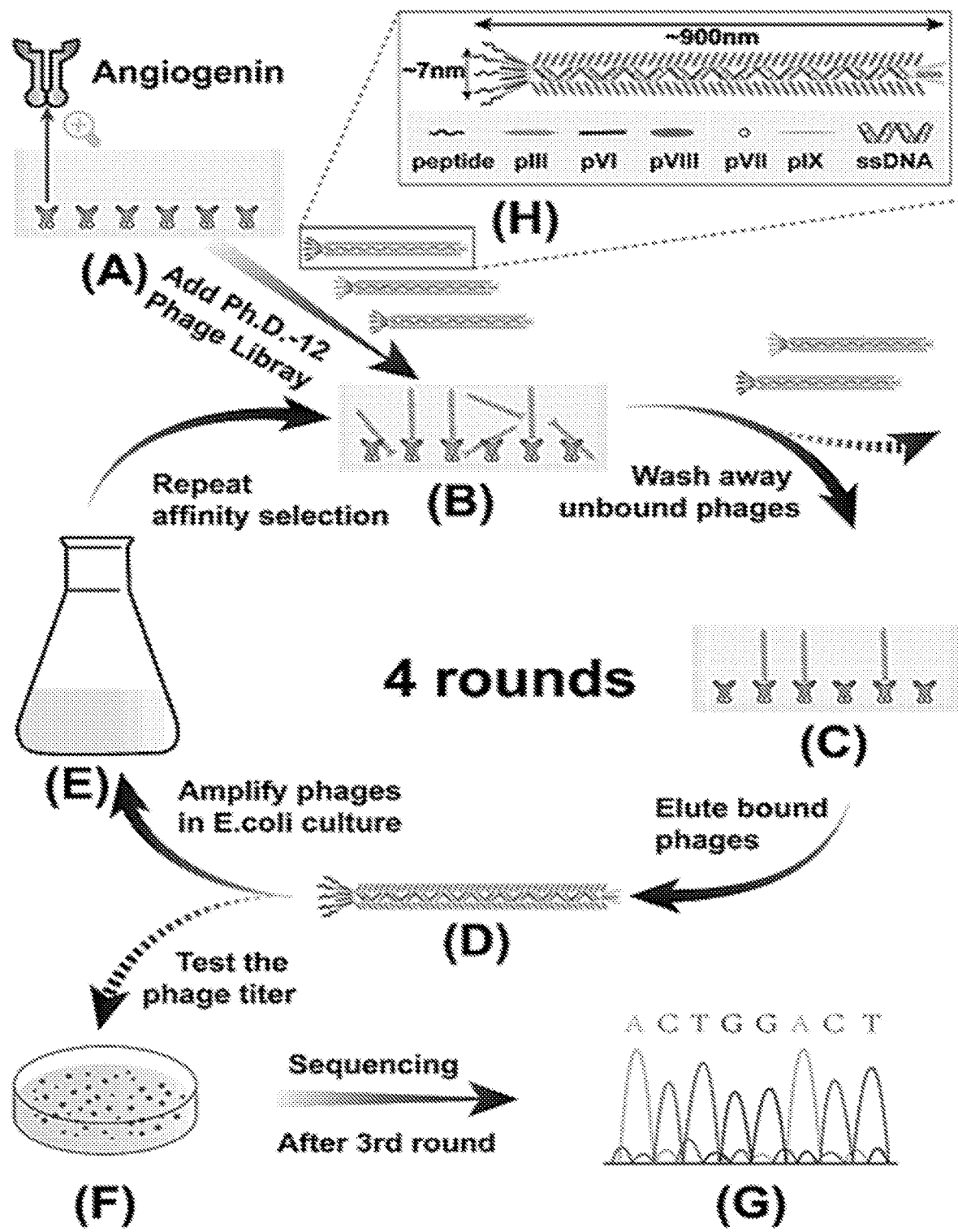
FIG. 1 shows a schematic of affinity-selection of angiogenin-binding peptides utilizing a Ph.D.-12 phage-displayed random peptide library: (a) angiogenin is coated on the cell culture plate; (b) the phage library is allowed to incubate with the angiogenin after the plate is blocked by the BSA; (c) angiogenin-bound phages bind the target and the non-bound phages are washed away; (d) the angiogenin-binding phages are eluted from the proteins; (e) the eluted phages are amplified by infecting the ER2738 E. coli host cells and used as a sub-library for the next round selection (B→C→D→E); (f) the eluted phages are used to process the titering assay by forming blue plaques in the Petri dish; (g) starting from the 3$^{rd}$ round, the plaques are sequenced to determine the consensus sequence, after the 4$^{th}$ round of selection, 57 plaques are picked out for DNA sequencing; and (h) the structure of an M13 phage in the phage library; a circular ssDNA is enclosed in a capsid made of five coat proteins (2700 copies pVIII constituting the side wall and five copies each of pIII, pVI, pVII and pIX capping one of the two terminals).

Anti-angiogenin (angiogenin-binding) peptides, and compositions carrying or containing the peptides are disclosed, including human-safe phages or nanoparticles equipped with both tumor-homing peptides and the anti-angiogenin peptides for use in anti-tumor therapies. Therapeutic compositions containing the angiogenin-binding peptides disclosed herein may be used, without a tumor homing peptide, for treating angiogenin-associated conditions, diseases, and disorders, such as the angiogenesis associated with diabetic retinopathy, age-related macular degeneration, retinopathy of prematurity, retinal artery or vein occlusion, corneal graft rejection, corneal neovascularization, neovascular glaucoma, uveitis, retinitis pigmentosa, sickle cell retinopathy, or other retinopathies.

Tumor-homing peptides, when comprising portions of the compositions, cause the carrier molecules or particles such as phages to be localized and enriched in tumors where the angiogenin-binding peptides capture and inactivate angiogenin molecules thereby blocking their angiogenic activity, inhibiting angiogenesis, and starving the tumor to death. Current cancer treatments by anti-angiogenic agents are limited by side effects in non-cancerous tissues due to a lack of tumor targeting capability of the agents. In one embodiment, the anti-angiogenin peptides disclosed herein can be employed, along with tumor homing agents, in compositions which directly home to targeted tumor tissues, thereby causing localization of the anti-angiogenin peptides. Examples of such tumor targeting (tumor homing) peptides include, but are not limited to, those shown in International Publication WO 2018/183232 and in U.S. Pat. Nos. 8,541,543; 8,710,017; 9,562,083; 9,657,077; 9,809,622; and 10,179,801, each of which is expressly incorporated by reference herein in its entirety. In one embodiment, both the anti-angiogenin peptides and the tumor homing peptides can be expressed in a genetically engineered phage nanofiber, such that the angiogenin-binding peptide is displayed, e.g., on the side walls, and the tumor-homing peptide is displayed, e.g., at the tips of the fiber. The resulting double-displayed dual-functional phage nanofiber can then home to the tumor, such as a breast tumor, and significantly inhibit the tumor angiogenesis and the subsequent tumor growth.

In one non-limiting example, a filamentous phage, such as a filamentous bacteriophage fd can be used. The fd phage may be a monodispersed fd388 phage. This phage is a nanofiber-like virus that contains a circular ssDNA core (including 11 genes) surrounded by a shell of genetically modifiable coat proteins (~3900 copies of pVIII array on the side wall, five copies each of pIII, pVI and pVII, pIX at the two tips) (Wang, Y., et al. Ultrasensitive rapid detection of human serum antibody biomarkers by biomarker-capturing viral nanofibers. *ACS Nano* 9, 4475-4483, 2015). The phage display has been widely utilized as a powerful tool to process the diagnosis and therapy in local clinics (Yang, M., Sunderland, K. & Mao, C. Virus-Derived Peptides for Clinical Applications. *Chem. Rev.* 117, 10377-10402, 2017). The tumor-homing peptide can be displayed on the pIII proteins at the tips of the nanofibers, enabling the nanofibers to be preferentially guided to the tumors. The angiogenin-binding peptides fused to the pVIII proteins of the phage nanofibers will then scavenge angiogenin secreted by the tumor, whereby hundreds of angiogenic molecules can be captured and inactivated by the angiogenin-binding peptides on the surface of each phage virus.

Before further describing various embodiments of the compositions and methods of the present disclosure in more detail by way of exemplary description, examples, and results, it is to be understood that the embodiments of the present disclosure are not limited in application to the details of methods and compositions as set forth in the following description. The embodiments of the compositions and methods of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. All of the compositions and methods of production and application and use thereof disclosed herein can be made and executed without undue experimentation in light of the present disclosure. While the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein, including, but not limited to, U.S. Provisional Application Ser. No. 62/655,357, filed Apr. 10, 2018, and International Publication WO 2018/183232, filed as PCT/US2018/024428.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. Any two values within the above ranges, e.g., 88 and 444 therefore can be used to set the lower and upper boundaries of a range (e.g., 88-444) in accordance with the embodiments of the present disclosure.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure, "substantially pure," or "isolated" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure. Where used herein the term "high specificity" refers to a specificity of at least 90%, or at least 91%, or at least 92%, or at least 93%, or at least 94%, or at least 95%, or at least 96%, or at least 97%, or at least 98%, or at least 99%. Where used herein the term "high sensitivity" refers to a sensitivity of at least 90%, or at least 91%, or at least 92%, or at least 93%, or at least 94%, or at least 95%, or at least 96%, or at least 97%, or at least 98%, or at least 99%.

The terms "subject" and "patient" are used interchangeably herein and will be understood to refer to a warm-blooded animal, particularly a mammal or bird. Non-limiting examples of animals within the scope and meaning of this term include dogs, cats, rats, mice, guinea pigs, horses, goats, cattle, sheep, zoo animals, Old and New World monkeys, non-human primates, and humans.

"Treatment" refers to therapeutic treatments. "Prevention" refers to prophylactic treatment measures to stop a condition from occurring. The term "treating" refers to administering the composition to a patient for therapeutic purposes, and may result in an amelioration of the condition or disease.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable biochemical and/or therapeutic effect, for example without excessive adverse side effects (such as toxicity, irritation and allergic response) commensurate with a reasonable benefit/risk ratio when used in the manner of the inventive concepts. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

The following abbreviations may be used herein for amino acids: alanine:ala:A; arginine:arg:R; asparagine:asn:N; aspartic acid:asp:D; cysteine:cys:C; glutamic acid:glu:E; glutamine:gln:Q; glycine:gly:G; histidine:his:H; isoleucine:ile:I; leucine:leu:L; lysine:lys:K; methionine:met:M; phenylalanine:phe:F; proline:pro:P; serine:ser:S; threonine:thr:T; tryptophan:trp:W; tyrosine:tyr:Y; and valine:val:V.

The term "peptide" is used herein to designate a series of amino acid residues, connected one to the other typically by peptide bonds between the alpha-amino and carbonyl groups of the adjacent amino acids to form an amino acid sequence. In certain embodiments, the peptides can range in length from 2 to 10 to 15 to 25 to 40 to 60 to 75 to 100 amino acids, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids. The term "polypeptide" or "protein" is used herein to designate a series of amino acid residues, connected one to the other typically by peptide bonds between the alpha-amino and carbonyl groups of the adjacent amino acids, wherein the length is longer than a single peptide. A peptide conjugate refers, in a non-limiting embodiment, to a compound comprising a peptide of the present disclosure which is conjugated (e.g., covalently linked, directly or indirectly via a linker sequence) to another molecule, such as a carrier molecule such as a protein or other polymeric molecule, e.g., a serum albumin molecule or antibody, or other therapeutic compound such as a drug, or an imaging or diagnostic moiety and wherein the peptide retains its activity (e.g., binding, targeting, imaging, or inhibitory) even when conjugated to the molecule. A "fusion protein" or "fusion polypeptide" refers to proteins or polypeptides (and may be used interchangeably) which have been created by recombinant or synthetic methods to combine peptides in a serial configuration. The peptides of the present disclosure may be produced using any nucleotide sequence which encodes the desired amino acid sequence. Any of the peptides described herein or active variants thereof may be used to make the peptide conjugates of the present disclosure.

Peptides of the present disclosure and the nucleic acids which encode them include peptide and nucleic acid variants which comprise substitutions (conservative or non-conservative) of the native amino acids or bases. For example, the peptide variants include, but are not limited to, variants that are not exactly the same as the sequences disclosed herein, but which have, in addition to the substitutions explicitly described for various sequences listed herein, additional substitutions of amino acid residues (conservative or non-conservative) which substantially do not impair the activity or properties of the variants described herein. Examples of such conservative amino acid substitutions may include, but are not limited to, ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met.

One of ordinary skill in the art would readily know how to make, identify, select or test such variants for receptor targeting activity against the same receptors targeted by the native peptides. Particular examples of conservative amino acid substitutions include, but are not limited to, gly:ala substitutions; val:ile:leu substitutions; asn:glu:his substitutions; asp:glu substitutions; ser:thr:met substitutions; lys:arg:his substitutions; and phe:tyr:trp substitutions. Other types of substitutions, variations, additions, deletions and derivatives that result in functional variant peptides are also encompassed by the present disclosure, and one of skill in the art would readily know how to make, identify, or select such variants or derivatives, and how to test for receptor binding activity of those variants.

The term "homologous" or "% identity" as used herein means a nucleic acid (or fragment thereof) or a peptide having a degree of homology to the corresponding natural reference nucleic acid or peptide that may be in excess of 60%, or in excess of 65%, or in excess of 70%, or in excess of 75%, or in excess of 80%, or in excess of 85%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%, or other specific percentages described herein. For example, in regard to peptides, the percentage of homology or identity as described herein is typically calculated as the percentage of amino acid residues found in the smaller of the two sequences which align with identical amino acid residues in the sequence being compared, when four gaps per 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877.

In at least one embodiment "% identity" represents the number of amino acids or nucleotides which are identical at corresponding positions in two sequences of a peptide or nucleic acids encoding similar peptides. For example, two amino acid sequences each having 15 residues will have at least 60% identity when at least 9 of the amino acids at corresponding positions are the same, at least 66% identity when at least 10 of the amino acids at corresponding positions are the same, at least 73% identity when at least 11 of the amino acids at corresponding positions are the same, at least 80% identity when at least 12 of the amino acids at corresponding positions are the same, at least 86% identity when at least 13 of the amino acids at corresponding positions are the same, and at least 93% identity when at least 14 of the amino acids at corresponding positions are the same. In another example, two amino acid sequences each having 19 residues will have at least 73% identity when at least 14 of the amino acids at corresponding positions are the same, at least 78% identity when at least 15 of the amino acids at corresponding positions are the same, at least 84% identity when at least 16 of the amino acids at corresponding positions are the same, at least 89% identity when at least 17 of the amino acids at corresponding positions are the same, and at least 94% identity when at least 18 of the amino acids at corresponding positions are the same.

Similarly, two amino acid sequences each having 20 residues will have at least 95% identity when 19 of the amino acids at corresponding positions are the same, or at least 90% identity when at least 18 of the amino acids at corresponding positions are the same, or at least 85% identity when at least 17 of the amino acids at corresponding positions are the same, or at least 80% identity when at least 16 of the amino acids at corresponding positions are the same. In other non-limiting examples, two amino acid sequences each having 100 residues will have 95% identity when 95 of the amino acids at corresponding positions are the same. Two amino acid sequences each having 100 residues will have at least 90% identity when at least 90 of the amino acids at corresponding positions are the same. Further, where a sequence is described herein as having "at least X % identity to" a reference sequence, this is intended to include, unless indicated otherwise, all percentages greater than X %, such as for example, (X+1)%, (X+2)%, (X+3)%, (X+4)%, and so on, up to 100%.

The terms "polynucleotide sequence" or "nucleic acid," as used herein, include any polynucleotide sequence which encodes a peptide product including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. The peptide may be expressed using polynucleotide sequence(s) which differ in codon usage due to the degeneracies of the genetic code or allelic variations.

The terms "infection," "transduction," and "transfection" are used interchangeably herein and mean introduction of a gene, nucleic acid, or polynucleotide sequence into cells such that the encoded peptide or protein is expressed. The polynucleotides which encode peptides or proteins of the present disclosure may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of the present disclosure.

In certain embodiments, the present disclosure includes expression vectors capable of expressing one or more peptide molecules described herein. Expression vectors for different cell types are well known in the art and can be selected without undue experimentation. Generally, the DNA encoding the fusion polypeptide is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Guidance can be found e.g., in Sambrook et al. Molecular Cloning: A Laboratory Manual, 3d ed., Cold Spring Harbor Laboratory Press, NY 2001)).

In at least certain embodiments, the peptide composition (also referred to herein as a peptide conjugate) of the present disclosure, whether wholly or partially synthetically or recombinantly produced, may be used as a pharmaceutical composition when combined with a pharmaceutically acceptable carrier. Such a composition may contain, in addition to the peptide conjugate and carrier, diluents, fillers, salts, buffers, stabilizers, solubilizers, and other materials well known in the art. Suitable carriers, vehicles and other components of the formulation are described, for example, in Remington: The Science and Practice of Pharmacy, $22^{nd}$ ed. The term "pharmaceutically acceptable" means a non-toxic material that does not interfere with the effectiveness of the biological activity of the peptide conjugate. The characteristics of the carrier will depend on the route of administration.

The pharmaceutical compositions of the present disclosure may be in the form of liposomes in which the peptide conjugate is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

An effective amount of the peptide conjugate used herein for treatment of a particular condition can be determined by the attending diagnostician, as one skilled in the art, by the use of conventional techniques and by observing results obtained under analogous circumstances. In determining the therapeutically effective dose, a number of factors may be considered by the attending diagnostician, including, but not limited to: the species of the subject; its size, age, and general health; the response of the individual subject; the mode of administration; the bioavailability characteristic of the preparation administered; the dose regimen selected; the use of concomitant medication; and other relevant circumstances. An effective amount of a peptide conjugate of the present disclosure also refers to an amount of the peptide conjugate which is effective in controlling or reducing the particular condition.

An effective amount of a composition of the present disclosure will generally contain sufficient active ingredient (i.e., the peptide conjugate) to deliver from about 0.1 µg/kg to about 100 mg/kg (weight of active ingredient/body weight of patient). Particularly, the composition will deliver at least 0.5 µg/kg to 50 mg/kg, and more particularly at least 1 µg/kg to 10 mg/kg. Without wishing to be held to a specific dosage, it is contemplated that the various pharmaceutical compositions used to practice the method of the present disclosure may contain, but are not limited to, about 0.01 mg to about 25 mg of the peptide conjugate per kg body weight per dose.

Practice of the method of the present disclosure may include administering to a subject an effective amount of the peptide conjugate in any suitable systemic or local formulation, in an amount effective to deliver the dosages listed above. In one embodiment, an effective, particular therapeutic dosage of the peptide conjugate is 1 µg/kg to 10 mg/kg. The dosage can be administered on a one-time basis, or (for example) from one to five times per day or once or twice per week, or continuously via a venous drip, depending on the desired therapeutic effect. In one therapeutic method of the present disclosure, the peptide conjugate is provided in an IV infusion in the range of from 1 mg/kg-10 mg/kg of body weight once a day. The duration of an intravenous therapy using the pharmaceutical composition of the present disclosure will vary, depending on the condition being treated and the condition and potential idiosyncratic response of each individual patient. In at least one embodiment, it is contemplated that the duration of each application of the peptide conjugate may be in the range of 1 to 4 hours and given once every 12 or 24 hours by continuous intravenous administration. Other therapeutic drugs, intravenous fluids, cardiovascular and respiratory support could also be provided if requested by the attending physician in a manner known to one of ordinary skill in the art.

In practicing the method of treatment or use of the peptide conjugates of the present disclosure, an effective amount of the peptide conjugate is administered to a mammal having a condition to be treated, such as a breast cancer tumor or any other cancer to which the peptide conjugate binds with high specificity. The peptide conjugate may be administered in accordance with the method of the present disclosure either alone or in combination with other therapies.

Administration of the peptide conjugate used in the pharmaceutical composition or to practice the method of the present disclosure can be carried out in a variety of conventional ways, such as, but not limited to, orally, by inhalation, rectally, or by cutaneous, subcutaneous, intraperitoneal, vaginal, or intravenous injection. In certain embodiments, oral formulations may be formulated such that the peptide conjugate passes through a portion of the digestive system before being released, for example it may not be released until reaching the small intestine, or the colon.

When an effective amount of the peptide conjugate is administered orally, the compound may be in the form of a tablet, capsule, powder, solution or elixir. The pharmaceutical composition may additionally contain a solid carrier such as a gelatin or an adjuvant. The tablet, capsule, and powder particularly contains from about 0.05 to 95% of the peptide compound by dry weight. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, 35 propylene glycol or polyethylene glycol. When administered in liquid form, the pharmaceutical composition particularly contains from about 0.005 to 95% by weight of peptide. For example, a dose of 10-1000 mg once to twice a day could be administered orally.

For oral administration, the peptide conjugates can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the peptide conjugates of the present disclosure can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the peptide conjugate in an aqueous or non-aqueous pharmaceutically acceptable solvent which may also contain suspending agents, sweetening agents, flavoring agents, and preservative agents as are known in the art.

For parenteral administration, for example, the peptide conjugates may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

When an effective amount of the peptide conjugate is administered by intravenous, cutaneous or subcutaneous injection, the peptide conjugate may be in the form of a pyrogen-free, parenterally acceptable aqueous solution or suspension. The preparation of such parenterally acceptable peptide solutions, having due regard to pH, isotonicity, stability, and the like, is within the skill in the art. A particular pharmaceutical composition for intravenous, cutaneous, or subcutaneous injection may contain, in addition to the peptide conjugate, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical compositions of the present disclosure may also contain stabilizers, preservatives, buffers, antioxidants, or other additive known to those of skill in the art.

As noted above, the compositions can also include an appropriate carrier. For topical use, any of the conventional excipients may be added to formulate the peptide compound into a lotion, ointment, powder, cream, spray, or aerosol. For surgical implantation, the peptide conjugate may be combined with any of the well-known biodegradable and bio-erodable carriers, such as polylactic acid and collagen formulations. Such materials may be in the form of solid implants, sutures, sponges, wound dressings, and the like. In any event, for local use of the materials, the peptide conjugate is usually present in the carrier or excipient in a weight ratio of from about 1:1000 to 1:20,000, but is not limited to ratios within this range. Preparation of compositions for local use is detailed in Remington: The Science and Practice of Pharmacy, $22^{nd}$ ed.

As noted, particular amounts and modes of administration are able to be determined by one skilled in the art. One skilled in the art of preparing formulations can readily select the proper form and mode of administration depending upon the particular characteristics of the peptide conjugate selected, the condition to be treated, and other relevant circumstances using formulation technology known in the art, described, for example, in Remington: The Science and Practice of Pharmacy, $22^{nd}$ ed. The pharmaceutical compositions of the present disclosure can be manufactured utilizing techniques known in the art. As noted above, typically the effective amount of the peptide conjugate will be admixed with a pharmaceutically acceptable carrier.

Additional pharmaceutical methods may be employed to control the duration of action of the peptide conjugate. Increased half-life and controlled release preparations may be achieved through the use of polymers to conjugate, complex with, or absorb the peptide conjugates described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, proteins (e.g., bovine serum albumin or human serum albumin) and the appropriate concentration of macromolecules as well as the methods of incorporation, in order to control release.

Another possible method useful in controlling the duration of action by controlled release preparations and half-life is incorporation of the peptide conjugate into particles of a polymeric material such as polyesters, polyamides, polyamino acids, hydrogels, poly(lactic acid), ethylene vinylacetate copolymers, copolymer micelles of, for example, PEG and poly(1-aspartamide).

It is also possible to entrap the peptide conjugates in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are well known to persons having ordinary skill in the art.

When the peptide composition is to be used as an injectable material, it can be formulated into a conventional injectable carrier. Suitable carriers include biocompatible and pharmaceutically acceptable phosphate buffered saline solutions, which are particularly isotonic.

For reconstitution of a lyophilized product in accordance with the present disclosure, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field. The pharmaceutical composition may also be in the form of an aqueous solution containing many of the same substances as described above for the reconstitution of a lyophilized product.

In certain embodiments the peptide conjugates of the present disclosure can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the peptide compositions (conjugates) of the present disclosure may be incorporated into pharmaceutical preparations which may be used for therapeutic purposes. However, the term "pharmaceutical preparation" is intended in a broader sense herein to include preparations containing a peptide composition in accordance with present disclosure, used not only for therapeutic purposes but also for reagent, imaging, or diagnostic purposes as known in the art. The pharmaceutical preparation intended for therapeutic use should contain a "pharmaceutically acceptable" or "effective amount" of the peptide compound, i.e., that amount necessary for a therapeutic response in a patient or subject in need of such treatment. If the pharmaceutical preparation is to be employed as a reagent, imaging, or diagnostic, then it should contain reagent, imaging, or diagnostic amounts of the peptide conjugates.

In certain non-limiting embodiments of the present disclosure, the peptide composition disclosed herein includes a filamentous bacteriophage, also referred to herein as a "phage," comprises a matrix of proteins encapsulating a genome encoding one or more fusion proteins (protein) is utilized. Examples of filamentous phages that may be used herein include, but are not limited to, M13, fl and fd phages. The fusion protein comprises an exogenous polypeptide portion (peptide) fused to the amino terminus of a coat protein of the filamentous phage. By "exogenous" is meant that the polypeptide portion fused to the phage protein is not normally associated with the phage protein in wild-type varieties of filamentous phage, but rather are foreign to the normal phage protein. The filamentous phage may encapsulate a genome which encodes a first and second fusion protein, where the first fusion protein comprises a first exogenous polypeptide portion fused to pVIII protein on the side wall and the second fusion protein comprises a second exogenous polypeptide portion fused to pIII, pVI, pVII and/or pIX proteins. The filamentous phage will further contain the fusion protein(s) displayed on the surface of the phage particle, as described elsewhere herein. Thus, where there are first and second fusion proteins, the phage can display these proteins in a function manner such that the first peptide serves as an angiogenin-binding peptide and the second peptide serves as a tumor-homing peptide. A "phagemid" or "phage vector" is a cloning and expression vector that contains components derived from both phage chromosomes and exogenous DNA such as that from plasmids. As the phagemid contains a portion of a phage genome, upon co-infection of the host with a helper phage, it can be packaged into phage particles. The phagemid or phage vector has been manipulated by insertion or incorporation of heterologous DNA, such as nucleic acid encoding the fusion proteins herein or expression cassettes provided herein. Such expression vectors typically contain a promoter sequence for efficient transcription of the inserted nucleic acid in the host cell. Examples of how exogenous peptides or polypeptides are bound or fused to phage proteins are shown in non-limiting examples in U.S. Pat. Nos. 7,078,166; 8,361,458; 8,728,985; and 9,446,122, each of which is incorporated herein in its entirety by reference.

Anti-angiogenin peptides of the present disclosure include, but are not limited to, amino acid sequences which include the 12-amino acid sequences shown in Table 1, or variants of the peptides of Table 1 as discussed in further detail elsewhere herein. The peptide may optionally further comprise an amino acid linker sequence of, for example, 1 to 100 additional amino acids.

TABLE 1

Sequences of selected anti-angiogenin-binding peptides

| Amino Acid Sequence | SEQ. ID NO |
|---|---|
| WPYWNHHSHNNV | 1 |
| FHHPSIHDRHRH | 2 |
| WHSPWRSWEVRS | 3 |
| HYNKLHKPRILY | 4 |
| GHSWHFHGRSPH | 5 |
| HWTPHNHWRLSR | 6 |
| FPDHFFWRLHRS | 7 |
| EHWRWPWQNLWR | 8 |
| WPNHHHHPRAHT | 9 |
| VDASHRLHWRLK | 10 |
| GYSHKHFFTSKR | 11 |
| WPRSSHHWYQHT | 12 |
| WPYHRSHAHPHP | 13 |
| STGHWHRSHFHF | 14 |
| HPMHMLHKRQHG | 15 |
| HLFTRHPHYGFQ | 16 |
| HFFNPHKALHSK | 17 |
| FHKTGNLINPRW | 18 |
| DMILAHTSGSIF | 19 |
| GANDGVSLWRNV | 20 |
| WHKTPLYTVKGP | 21 |
| FNPPRATWLGTY | 22 |
| GPWKQHKHWLYA | 23 |
| WPHNHWRNQAPS | 24 |
| WIPRHWHEHLVT | 25 |
| HSWXSWXLQNRX | 26 |
| QVNGLGERSQQM | 27 |
| GWWHPKAPPPKP | 28 |
| LTGGHLHGSVRH | 29 |
| LEQPGHSVLSHR | 30 |
| WSWHGLDWRWRS | 31 |
| HMTAWHQHRSNT | 32 |
| GPFKMHRWLPHT | 33 |
| NHFTLTRHTHYK | 34 |
| GPHYYHPWKHRA | 35 |
| WPTHSHRGYFFV | 36 |
| SHWSSYFHPRGN | 37 |
| GFFDKHRSWHIT | 38 |
| HIKWNISNSIST | 39 |
| WDVHSXLGHRXX | 40 |
| HHFSKLPLKHSH | 41 |
| RDYHPRDHTATW | 42 |
| WHRDFFPQSFRS | 43 |
| HGSFHWRTHGLX | 44 |

Tumor-homing peptides of the present disclosure include, but are not limited to, amino acid sequences which include the 15-amino acid sequences shown in Table 2, or variants of the peptides of Table 2 as discussed in further detail in International Publication WO 2018/183232. The peptide may optionally further comprise an amino acid linker sequence of, for example, 1 to 50 additional amino acids.

TABLE 2

Selected tumor-homing peptides*.

| Amino Acid Sequence | SEQ ID NO: |
|---|---|
| AREYGTRFSLIGGYR | 45 |
| PKAFQYGGRAVGGLW | 46 |
| PVRYGFSGPRLAELW | 47 |
| RNVPPIFKEVYWIAQ | 48 |
| RTLIRMGTGAHAFAV | 49 |

*SEQ ID NOS: 1-5 in International Publication WO 2018/183232

Examples of particles, drugs, reagents, imaging, and/or diagnostic agents that may be conjugated, directly or indirectly, to, or which may express, the peptides disclosed herein include, but are not limited to:
(a) nanoparticles, such as viral nanoparticles including phages, viruses, and virus fragments;
(b) chemotherapeutic drugs including those having suitable sites for linking directly to or via a linker to the peptide, wherein the drug has activity while still conjugated to the peptide, or becomes active upon release from the peptide at the tumor site; for example the linker can be an acid-labile linker, an ester linker or a carbamate linker, and the drug can be, for example, doxorubicin or taxol, or any other drug which can be linked to the peptide;
(c) diagnostic reagents, such as radioisotopes for PET imaging, quantum dots, and near-infrared red excited dye for fluorescence imaging, and magnetic nanoparticles such as iron oxide for MRI;
(d) oligonucleotides (DNA or RNA) or oligopeptides can be used as detectable reagent for diagnosis or anti-cancer reagent to interfere cancer cell behavior;

(e) drug carriers including nano-carriers (nano-cages, nano-dendrites and etc.), liposomes, polymeric drug scaffolds and polymeric micelles those are able to load, transport and release drugs; and (f) functional particles such as gold-nanorods and gold-nanoparticles, or photosensitizer reagents such as aminolevulinic acid (ALA), and Silicon Phthalocyanine, for example, which are sensitive to either wide spectrum or specific wavelength laser that can be used for photothermal therapy and Photodynamic therapy (PDT).

In at least one embodiment of the present disclosure, the anti-angiogenin peptide comprises an amino acid sequence which includes the 12-amino acid sequence WPYWNHHSHNNV (SEQ ID NO:1), or variants thereof. The peptide may optionally comprise an amino acid linker sequence of, for example, 1 to 100 additional amino acids such that the peptide comprises or consists of 13-112 total amino acids (e.g., 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids), or more particularly 13-50 amino acids (e.g., 13, 14, 15, 16, 17, 18, 19, 20, 21, 22, 23, 24, 25, 26, 27, 28, 29, 30, 31, 32, 33, 34, 35, 36, 37, or 38), including SEQ ID NO: 1 or variants thereof. In the peptides which include SEQ ID NO:1 or variants thereof, and a linker sequence, the linker sequence may extend from the N-terminal or C-terminal end of the amino acid sequence SEQ ID NO:1, or variant thereof. The amino acids of the linker sequence, or the substituted amino acids of the SEQ ID NO:1 variant may be selected from, but are not limited to, the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val. In certain embodiments, the peptides of the present disclosure include variants of SEQ ID NO:1 which may include substitutions, such as conservative substitutions, or any amino acid in a D or L configuration (such as listed above), wherein the variant peptide has the activity of the non-variant version of the peptide. Examples of substitutions include but are not limited to those described elsewhere herein. Examples of substitutions include but are not limited to those described elsewhere herein. In at least certain embodiments, the variant peptides of SEQ ID NO:1 comprises at least at least 83% or greater sequence identity (as defined elsewhere herein) with SEQ ID NO:1, i.e., it is identical except for one or two amino acid substitutions.

As noted, in a fusion protein present on a phages described herein, the "fusion" between the exogenous polypeptide portion and the filamentous phage protein may comprise a typical amide linkage, or may comprise a linker peptide or polypeptide (i.e., a "linker") as described herein. For example, any of a variety of linkers may be used which are typically a stretch of about 5 to 50 amino acids in length. Linkers desirably provide a high degree of mobility (flexibility) to the fusion protein at the point of the linker. An exemplary, non-limiting, linker has the formula -(Gly$_4$Ser)$_n$-, where n=1-10, (SEQ ID NO:50).

In at least one embodiment of the present disclosure, the anti-angiogenin peptide comprises an amino acid sequence which includes the 12-amino acid sequence FHHPSIHDRHRH (SEQ ID NO:2), or variants thereof. The peptide may optionally comprise an amino acid linker sequence of, for example, 1 to 100 additional amino acids such that the peptide comprises or consists of 13-112 total amino acids (e.g., 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids), or more particularly 13-50 amino acids (e.g., 13, 14, 15, 16, 17, 18, 19, 20, 21, 22, 23, 24, 25, 26, 27, 28, 29, 30, 31, 32, 33, 34, 35, 36, 37, or 38), including SEQ ID NO: 2 or variants thereof. In the peptides which include SEQ ID NO:2 or variants thereof, and a linker sequence, the linker sequence may extend from the N-terminal or C-terminal end of the amino acid sequence SEQ ID NO:2, or variant thereof. The amino acids of the linker sequence, or the substituted amino acids of the SEQ ID NO:2 variant may be selected from, but are not limited to, the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val. In certain embodiments, the peptides of the present disclosure include variants of SEQ ID NO:2 which may include substitutions, such as conservative substitutions, or any amino acid in a D or L configuration (such as listed above), wherein the variant peptide has the activity of the non-variant version of the peptide. Examples of substitutions include but are not limited to those described elsewhere herein. Examples of substitutions include but are not limited to those described elsewhere herein. In at least certain embodiments, the variant peptides of SEQ ID NO:2 comprises at least 83% or greater sequence identity (as defined elsewhere herein) with SEQ ID NO:2, i.e., it is identical except for one or two amino acid substitutions.

In other embodiments of the present disclosure, the anti-angiogenin peptide comprises at least one of amino acid sequences of the group SEQ ID NO:3-44, or variants thereof. The peptide may optionally comprise an amino acid linker sequence of, for example, 13-112 total amino acids (e.g., 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, 60, 61, 62, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids), or more particularly 13-50 amino acids (e.g., 13, 14, 15, 16, 17, 18, 19, 20, 21, 22, 23, 24, 25, 26, 27, 28, 29, 30, 31, 32, 33, 34, 35, 36, 37, or 38), including said sequences or variants thereof. In the peptides which include said sequences or variants thereof, and a linker sequence, the linker sequence may extend from the N-terminal or C-terminal end of the said sequences, or variants thereof. The amino acids of the linker sequence, or the substituted amino acids of said sequence variant may be selected from, but are not limited to, the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val. In certain embodiments, the peptides of the present disclosure include variants of said sequences which may include substitutions, such as conservative substitutions, or any amino acid in a D or L configuration (such as listed above), wherein the variant peptide has the activity of the non-variant version of the peptide. Examples of substitutions include but are not limited to those described elsewhere herein. Examples of substitutions include but are not limited to those described elsewhere herein. In at least certain embodiments, the variant peptides of said sequences comprise at least 83% or greater sequence identity (as defined elsewhere herein) with said sequences, i.e., they are identical except for one or two amino acid substitutions.

Returning to the description, various embodiments of the present disclosure will be more readily understood by reference to the following examples and description, which as noted above are included merely for purposes of illustration of certain aspects and embodiments of the present disclosure, and are not intended to be limiting. The following detailed examples and methods describe how to make and use various peptides, peptide conjugates, and other peptide compositions of the present disclosure and are to be construed, as noted above, only as illustrative, and not limitations of the disclosure in any way whatsoever. Those skilled in the art will promptly recognize appropriate variations from the materials and procedures described herein.

Experimental

As described in further detail below, a dual-functional fd388-AR-WV phage (~1 um long and 7 nm wide) was constructed with a tumor-homing peptide AR (SEQ ID NO:45) displayed at the pIII end, and an angiogenin-binding peptide WV (SEQ ID NO:1) displayed on pVIII, for selectively homing to and being retained in breast tumors and for blocking angiogenin-blocking to inhibit tumor angiogenesis and subsequently inhibit tumor growth. Although the tumor-homing peptide used in the example was a breast cancer homing peptide, any tumor-homing peptide could be used in the angiogenin-binding peptide compositions considered herein.

Methods

Identification of Angiogenin-Binding Peptides by Affinity-Selection

Phage affinity-selection (biopanning) procedure was performed by following the standard protocol with minor modifications (FIG. 1). The target protein angiogenin (R&D systems, Inc., Minneapolis) used for biopanning was diluted to 20, 4, 0.8 and 0.16 µg/mL in 0.1 M NaHCO$_3$ (pH=8.6) in the first, second, third and fourth round, respectively. During each round, 400 µL of angiogenin with designated concentration, was added into a well (diameter is 15.6 mm) of the 24 well cell culture plate (Cat. #: 142475, Thermo Fisher Scientific), and incubated overnight at 4° C. with the lid on in a humidified container. Then the supernatant was pipetted out and the plate was firmly slapped face down on a paper towel to remove the residual solution. Afterwards, 500 µL of blocking buffer (5 mg/mL BSA, 0.1M NaHCO$_3$) was added into the well and incubated for 3 h at 4° C., after which the supernatant was discarded. Then 500 µL of 0.5% PBST buffer (0.5% Tween 20 in phosphate buffered saline (PBS) buffer) was added into the well and incubated on a rocking shaker for 10 min at room temperature, then poured off and slapped face down on a new paper towel, followed by washing the plate 6 times. Following this, 10 µL of the Ph.D.-12 phage library solution (for the first round of selection, New England Biolabs) or 10$^9$ pfu (plaque forming units) of the amplified phage sub-library (from the previous round of selection for each subsequent round of selection) in 400 µL of 0.5% PBST buffer was added into the well and incubated in a humidified container for 2 h at room temperature. The supernatant was discarded and washed with PBST 6 times as above. Then 400 µL of 0.1 M elution buffer (0.1 N HCl, 1 mg/mL BSA, and pH adjusted to 2.2 with glycine) was added into the well and incubated for 10 min The mixture was pipetted into a sterile microcentrifuge tube and neutralized with 60 µL of 1 M Tris-HCl (pH=9.1) immediately.

Titer of a Phage Solution

A small amount (5 µL) of the above eluate mixture was diluted 10-fold with PBS buffer. A total of 10 µL of the diluted solution was incubated with 90 µL of mid-log E. coli strain ER2738 culture (OD$_{600}$=0.5) for 5 min. The infected ER2738 cells were transferred into 3 mL of 45° C. Top Agar in 10 mL sterile centrifuge tube and vortexed briefly to mix well, then were immediately spread onto a pre-warmed LB/IPTG/X-gal plate (0.05 mg/mL, 0.04 mg/mL). The plate was cooled for 10 min at room temperature, and inverted to incubate overnight at 37° C. The titer was calculated by this equation: titer=1000×N×M pfu/mL, where N and M are the dilution factor and the number of the blue phage plaques on a plate, respectively. After the third round of selection, 57 random plaques were picked out separately for DNA sequencing with the primer of 5'-CCCTCATAGT-TAGCGTAACG-3' (SEQ ID NO:51).

Amplification and Purification of Selected Phages

After titering, the remaining eluate phages were incubated with 20 mL of early-log ER2738 culture (0.01<OD$_{600}$<0.05) for 30 min at room temperature. The phage-infected bacterial were then incubated at 37° C. first for 20 min at 100 rpm stirring and afterwards another 4 h at 200 rpm. After the amplification, the cells were transferred into sterile tubes and centrifuged at 7,200 g for 10 min. The supernatant was transferred into a 250 mL flask, followed by adding 9 mL of a solution containing 16.7% PEG 8000 and 2.5 M NaCl (termed PEG/NaCl) and mixing thoroughly. The mixture was incubated at 4° C. overnight to allow phage precipitation. Then the mixture was centrifuged at 13,000 g for 30 min and the supernatant was decanted and discarded. The phage pellet was re-suspended into 1 mL of PBS. The phage solution was transferred to a new microcentrifuge tube and centrifuged again at 13,000 g for 30 min. Subsequently, the supernatant containing phage was transferred to a new microcentrifuge tube and mixed with 200 µL of the PEG/NaCl solution again, then incubated at 4° C. for 5 h. The resultant mixture was centrifuged at 13,000 g for 30 min and the phage pellet was dissolved in 200 µL of PBS.

Assay of Specificity of the Selected Phage Binding to Angiogenin

The high frequent clones, determined by DNA sequencing, were individually amplified and purified through procedures described in the previous section 2.3. Then we employed phage ELISA experiment to assay the affinity of the as-selected phages toward the angiogenin. The procedure is as the following. Firstly, 50 µL of 4 µg/mL angiogenin solution (diluted in 0.1 M NaHCO$_3$, pH=8.6) was added into a well of the 96-microwell plate and incubated overnight at 4° C. with the lid on in a humidified container, meanwhile, the same volume of PBS buffer and wild type phage were respectively added into another well as the blank control and negative control. Then the supernatant was pipetted out and the plate was firmly slapped face down on a paper towel to remove the residual solution. 200 µL of 0.5% BSA blocking buffer was added into the well and incubated for 1 h at 4° C., then the supernatant was discarded. Afterwards, 200 µL of 0.5% PBST buffer was added into the well and incubated on a rocking shaker for 3 min at room temperature, then poured off and slapped face down on a new paper towel, followed by washing the plate 5 times.

Following this, 50 µL of 2×10¹⁰ pfu/mL phage solution was added into the well and incubated in a humidified container for 1 h at room temperature. The supernatant was discarded and the plate was washed 6 times with PBST. Then 100 µL of diluted anti-M13 bacteriophage coat protein g8p antibody (Cat. #: ab9225, abcam) was incubated with the phage for 1 h at 4° C. and washed 3 times with PBST. And 100 µL of diluted Goat Anti-Mouse Secondary Antibody conjugated with HRP (Cat. #: ab6789, abcam) was added and incubated for 1 h at 4° C. The plate was washed 3 times with PBST, and firmly slapped face down on a paper towel to remove the residual solution. A total of 100 µL of TMB ELISA Substrate (Cat. #: ab171523, abcam) was added into each well and incubated until the blue reaction products appear, then the reaction was stopped immediately with 100 µL of 1M HCl solution. The absorbance of each well at 450 nm was then recorded and analyzed.

Peptide Computational Studies

The peptide-protein complex was generated using the online server, CABS-docking, which performs simulation search for the binding site(s) while allowing for full flexibility of the peptide and small fluctuations of the receptor backbone. The best docking model (based on the average ligand RMSD) from the CABS-dock results was chosen as the initial structure, which was solvated in 72 cubic Å box, to perform a 50 ns molecular dynamical (MD) simulation using NAMD on OU's supercomputing center (GPU node). Amber force field was used to model the protein and peptide. The MD simulation system was equilibrated at 300K for 2 ns. Periodic boundary conditions were used and long range electrostatic interactions were calculated with particle mesh Ewald method, with non-bonded cutoff set to 12.0 Å and SHAKE algorithm was used to constraint bonds involving hydrogen atoms. Time step is 2 fs and the trajectories were recorded every 10 ps.

Construction of Genetically Engineered Dual-Functional MCF-7 Tumor-Homing/Angiogenin-Binding Phages We exploited our double-display system to display two types of peptides on a single phage to form dual-functional phage particle. One was an MCF-7 breast tumor-homing peptide (AREYGTRFSLIGGYR, termed AR, SEQ ID NO:45; or PKAFQYGGRAVGGLW, termed PW, SEQ ID NO:46) fused to the tip of phage and another was the angiogenin-binding peptide fused to the side wall of the same phage to form the MCF-7 tumor-homing/angiogenin-binding phages.

Displaying of ANG-Binding Peptide on pVIII:

First, a pair of complementary nucleotides encoding angiogenin-binding peptide WV were designed and purchased from Invitrogen (Table 3).

TABLE 3

Nucleotides encoding angiogenin-binding peptide WV

| DNA Sequence* | SEQ ID NO: |
|---|---|
| 5'-<u>AGCTTT</u>GCCTGGCCTTATTGGAATCAT CATTCGCATAATAATGTGGGTGCA-3' | 52 |
| 5'-<u>CC</u>CCACATTATTATGCGAATGATGATTC CAATAAGGCCAGGCAA-3' | 53 |

*Boldface indicates angiogenin-binding peptide WPYWNHHSHNNV (SEQ ID NO: 1), underlining indicates sticky end of the HindIII and PstI restriction endonucleases.

Five µL of 100 µM of the two complementary nucleotides were added into 40 µL of sterile water and mixed well. Then the mixture was incubated at 94° C. for 5 min, and cooled down slowly to room temperature to anneal into double strand DNA fragment. Meanwhile, the fd388 RF phage vector, a vector was constructed by inserting the recombinant gene 3 of the fUSE55 vector into the f88-4 vector to replace the original wild-type gene 3, was double digested by HindIII and PstI at 37° C. overnight, and purified by agarose gel electrophoresis. The purified linear vector was ligated with the previously annealed DNA fragment by the T4 DNA ligase at 16° C. overnight to form recombinant plasmid (p-fd388-WV) which could encode the WV on the N-terminal of the pVIII of fd phage. This recombinant plasmid was then transferred into the competent E. coli JM109 bacterial cells. The positive JM109 clones with gene insertion were selected for DNA sequencing to confirm the correct insertion of gene encoding peptide WV. Displaying of MCF-7 tumor-homing peptide on pIII: The correct JM109 clones was then cultured in the LB under shaking at 37° C. overnight to amplify the recombinant p-fd388-WV. Then the p-fd388-WV was extracted using the QIAprep® Spin Miniprep Kit (Qiagen, US) and double digested by SfiI, followed by purification using agarose gel electrophoresis. Meanwhile the two complementary nucleotides encoding MCF-7 tumor-homing peptides and restrictive sites of SfiI on both ends (see Supplementary Table 2, U.S. Provisional Application Ser. No. 62/655,357) were anneal to form double strand as above procedure, respectively. Then the two annealed DNA fragments were ligated by T4 DNA ligase with the previously digested p-fd388-WV at 16° C. overnight, respectively, to form two types of double-display recombinant plasmids (p-fd388-AR-WV and p-fd388-PW-WV) which could encode the AR/PW on the N terminal of the pIII proteins, and WV on the N terminal of the pVIII proteins of fd phage. The two double-display plasmids were transformed into the competent E. coli JM109 bacterial cells, and the positive JM109 clones with gene insertion were selected for DNA sequencing to confirm the correct insertion of gene encoding AR/PW.

Amplification and Purification of Dual-Functional Phages

The dual-functional phages were amplified by following procedures: The E. coli JM109 strains containing the recombinant double-display recombinant plasmids were incubated in 10 mL of LB/streptomycin/tetracycline culture medium (50 mg/L, 20 mg/L) with overnight shaking at 37° C. The cell culture was centrifuged at 8000 g for 30 mM, and the supernatant containing dual-functional phage particles was transferred into 100 mL of the mid-log ($OD_{600}$=0.5) E. coli K91Kan cell culture and shaken at 100 rpm at 37° C. for 30 mM to infect the K91Kan cells. 100 µL of 20 mg/mL tetracycline and 100 µL of 1M IPTG was added into the mixture and shaken at 150 rpm for 3 h, then transferred into 1 L of LB/IPTG/ tetracycline culture medium (1 mM, 20 mg/L) and shaken at 150 rpm for another 12 h. The purification of the engineered phages was the same as above.

Silver Staining of SDS-PAGE

The phages were carried out the SDS-polyacrylamide gel electrophoresis (SDS-PAGE): 20 µg of each phage was mixed with the protein loading buffer and boiled for 5 min, then loaded into sample well of the 20% acrylamide gels containing 18% glycerol. After that, started electrophoresis was processed at 80 V voltage until the sample has gone through the stacking gel. Then the 120 V voltage was applied to the next step electrophoresis for 6 h. The gel was incubated with the fixing solution I (5% acetic/50% methanol) and II (5% acetic/5% methanol) for 1 h, respectively.

The gel was washed with water 3 times, then incubated into the 0.1% cold silver nitrate for 30 min and washed with water for seconds. After that, the developer (0.6% methanol/4% $Na_2CO_3$) was added into the gel to develop the protein bands. The development was stopped with 10% acetic acid immediately when the desired intensity observed. The silver stained gel was imaged under the Gel Doc™ EZ System.

Protein Dot Blotting Assay Between the Angiogenin and Displayed Phage

A total 5 μL of 20 μg/mL angiogenin was dropped on the nitrocellulose membrane (Cat. No. LC201, Invitrogen) and incubated at 37° C. until turning dry completely. The membrane was incubated with 0.5% BSA blocking solution for 1 h at 37° C., then washed 3 times with PBS solution. 200 μL of the displayed phage, WT phage and PBS were added respectively on the corresponding area and incubate for 1 h at 37° C., then washed 3 times with PBS solution. After that, the film was incubated with diluted anti-M13 Bacteriophage Coat Protein g8p antibody for 1 h at 37° C. and washed 3 times with PBS. Afterward, the film was incubated with diluted Goat Anti-Mouse Secondary Antibody conjugated with HRP and washed twice. Finally, 1 mL of the ECL Blotting Substrate (Cat. No. 3229, Thermo Fisher Scientific) was dropped on the film and imaged.

Cell Culture

MCF-7 cells, from a human mammary gland cell line derived from a metastatic site, were obtained from ATCC and cultured in Eagle's Minimum Essential Medium (Cat. #: 30-2003, ATCC) containing 10% fetal bovine serum (ATCC® 30-2020™). MCF-10A cell (ATCC® CRL-10317™), a non-tumorigenic epithelial cell line, were obtained from ATCC and culture in MEBM medium (Cat. #: 30-2003, ATCC) containing 10% fetal bovine serum 100 ng/ml cholera toxin and the MEGM kit (Cat. #: CC-3150, Lonza/Clonetics Corporation).

Establishment of MCF-7 Orthotopic Tumor-Bearing Mice Model

According to the National Cancer Institute's (NCI) experience, the orthotopic xenograft models are more useful for predicting the phase 2 clinical trial performance and remain as the primary choice of the pharmaceutical industry, comparing with the subcutaneous xenograft models in immunodeficient mice. So we established the human breast tumor orthotopic xenografts in immunodeficient mice using MCF-7 cancer cell lines following the procedures below to investigate the bio-distribution and therapeutic effect of our dual-functional phages. To increase the concentration of the estrogen level of a mouse, a 17β-Estrdiol pellet (0.36 mg/pellet, 60 day release, Innovative Research of America) was implanted subcutaneously on the lateral side of the neck between the ear and shoulder of the 4-week-old athymic nude mouse (Athymic Nude-Foxn1$^{nu}$/Foxn1$^{+}$, Harlan Lab) under 2% isoflurane (NDC: 11695-6776-2, Henry Schein Animal Health)/oxygen mixture (vt-110 small animal anesthesia machine). After the surgery, 50 μL of 2% lidocaine (NDC: 11695-4147-1, Henry Schein Animal Health) was subcutaneously injected into the surgical area immediately. 24 hours later, the mouse was anesthetized again using the same procedures and a small incision was made with a scissor between the midline and the fourth nipple. After cleaning with the cotton swab soaked in PBS, the mammary fat pad was exposed by a tweezer. Then a total of $5\times10^5$-$10^6$ MCF-7 cells suspended in 100 μL of PBS were injected into the mammary fat pad by 1-cc TB syringe with 21 G needle in a sterile hood. The incision was sutured and 50 μL of 2% lidocaine was subcutaneously injected into the surgical area immediately.

Hemolysis Assay of the Dual-Functional Phage

Blood compatibility of the dual-functional phage was evaluated through hemolysis experiment. 4 mL of the fresh blood was collected from the orbital sinus of several mouse into the 10 mL BD vacutainer® sodium heparin tube (REF 367874, BD, USA). The vacutainer tube was inverted several times and centrifuged for 5 min at 1000 rpm. The pellet RBSs (red blood cells) were washed 3 times with PBS solution, and resuspended with 20 mL PBS. Then 800 μL of dual-functional phage was added into 200 μL of the RBCs solution and incubated for 6 h at 37° C., while the 800 μL of the wild type phage was added into the 200 μL of cell as the control group, respectively. the samples were centrifuged at 4000 rpm for 5 min 200 μL of plasms supernatants was added into 3 mL of 0.01% $Na_2CO_3$ solution, and the OD values were recorded at 380, 415 and 450 nm. The plasma hemoglobin (Hb) was determined using Eq. 1. The percentage of hemolysis was calculated using Eq. 2.

$$Hb = [(2A415) - 76.25 \times (A380 + A450)] \quad \text{(Eq. 1)}$$

$$\text{Hemolysis (\%)} = Hb_{sample}/Hb_{water} \quad \text{(Eq. 2)}$$

To obtain 100% hemolysis, cells were lysed by the distilled water/deionized water and the positive control was obtained by treating with 0.9% saline.

Investigation of the bio-distribution of the dual-functional phages

When the diameter of the tumor reached about 0.5 cm which was about 18 days after the establishment of the MCF-7 tumor orthotopic xenograft models, 100 μL of the two double-displayed phages or wild type phage at $10^{10}$ pfu/mL was injected into the tail vein. After circulating for 4 h of phages in vivo, the mice were anesthetized again following the procedure in section 2.10. Then a small incision was made in the right atrium with a scissor, and 20 mL of PBS was injected into the left ventricular to completely remove all the blood in tissues. The tumor and important organs including heart, liver, spleen, lung and kidney, were harvested into the sterile PBS buffer. Then the phages were released from the tumor and organs, and titered by the following procedures: The weight of each organ was measured and then grinded completely to release the enriched phages. The grinded tissue fluid was serially diluted in 10-fold gradients. 10 μL of the each dilution was incubated with 90 μL mid-log E. coli K91Kan for 20 min at room temperature. The infected E. coli cell culture was transferred into 3 mL of 45° C. top agar, vortexed briefly to mix well, and spread immediately onto a pre-warmed LB/Kan plate (50 μg/mL). The plate was cooled for 10 min at room temperature, and inverted to incubate overnight at 37° C. The quantity of phages in one organ was calculated by the equation: quantity=D×N×1000/Q, where D, N and Q are the dilution factor, the number of blue phage plaques on a plate and the weight of an organ, respectively.

Inhibition of tumor growth in orthotopic xenografts mice by dual-functional phage In order to test if the dual-functional phage could influence the tumor growth, the fd388-AR-WV phage was injected into the tail vein on the 10$^{th}$ day, while several vessels formed in the tumor when the diameter of the tumor lager than 2 mm$^3$. And the tumor volume measured using digital caliper every 2 days and calculated using the equation: Volume=½×a×b$^2$ (a is the length and b is the width of the tumor). The mice were sacrificed and blood was removed. Tumors were excised and wet-weighed at the end of the experiment.

Immunohistochemical and Histochemical Assay

Tumor tissue was fixed in 4% paraformaldehyde 48 h, paraffin-embedded and prepared 5 μm sections on the glass slides. The section was heated at 60° C. for 2 h and deparaffinized in xylol and rehydrated in graded alcohol. Then the section was overlaid with 0.01 mol/L citrate antigen solution (pH=6.0) and incubated in saturated steam for 30 min to retrieve the antigen. Following this, the section was incubated in 0.5% BSA block solution for 1 h and washed 3 times with PBS, then stained with rabbit polyclonal anti-CD31 antibody (Cat. #: ab28364, abcam) for 1 h and washed with PBS. The section was stained with goat anti-rabbit secondary antibody (Cat. #: ab205718, abcam) for 1 h and washed with PBS, then incubated with HRP substrate solution (DAB) for 5-10 min and washed. Finally, the section was counterstained in Mayer's Hematoxylin (TA-060-MH, Thermo Fisher) for 5 min and washed with PBS. For assay the micro-vessels density, the sections were scanned at 40× magnification by using light microscope (0.644 mm$^2$ per field). The microvessel was defined as distinct CD31+ vessel lumen and cell cluster. The MVD (microvessl density) and vessel diameter were measured by using the Image-Pro software. Counting was performed in 3 respective field of per section. To study the intratumoral necrosis and the immunoreaction in main organ (heart, liver, and kidney), the tissues were harvested, fixed in paraformaldehyde and processed H &E staining. The deparaffinized sections were incubated with Hematoxylin for 10 min and wash with H$_2$O, then incubated with Eosin (catalog No. 7111, Thermo fisher) for 10 min Finally, the sections were scanned 20× magnification by using light microscope.

Cytotoxicity and Cell Viability Assay

MCF-7 and MCF-10A cells were cultured in 96-well culture plates containing medium and 5% FBS for 12 h, then 100 μL of FBS-free medium containing 10$^9$ pfu of phage was added into the well to continue incubate for 24 h. Following this, 100 μL of LIVE/DEAD Cell Imaging Kit (Cat. #: R37601, Invitrogen) solution was added into each well and incubated for 20 min. Then, the plate was scanned using fluorescence microscope. On the other hand, 10 μL of the alamarBlue solution (BUF012B, Bio-rad) was added into each well, after the MCF-7 and MCF-10A cell were treat with 10$^9$ pfu of phage. Finally, the plate was measured at 570 nm and 600 nm on a microplate reader when the color changed. Each assay was repeat 5 times. The cell viability was calculated using equation Eq. 3:

$$\text{Cell viability} = 117216 \times A_{570\,nm} - 80586 \times A_{600\,nm} \quad (\text{Eq. 3})$$

Statistical Analysis

All data are presented using the mean±standard deviation (SD). The differences with the P<0.05 and P<0.01 were considered significant and extremely significant. The in vitro experiments were performed in 4 independent repeats. Animal studies were performed with 5-6 mice in each group. Statistical analysis was performed using OriginPro 9 software. One-Way ANOVA was used for multiple comparisons as described in the figure legends.

Results

Biopanning of the Phage Library Against Angiogenin

Figure 2:
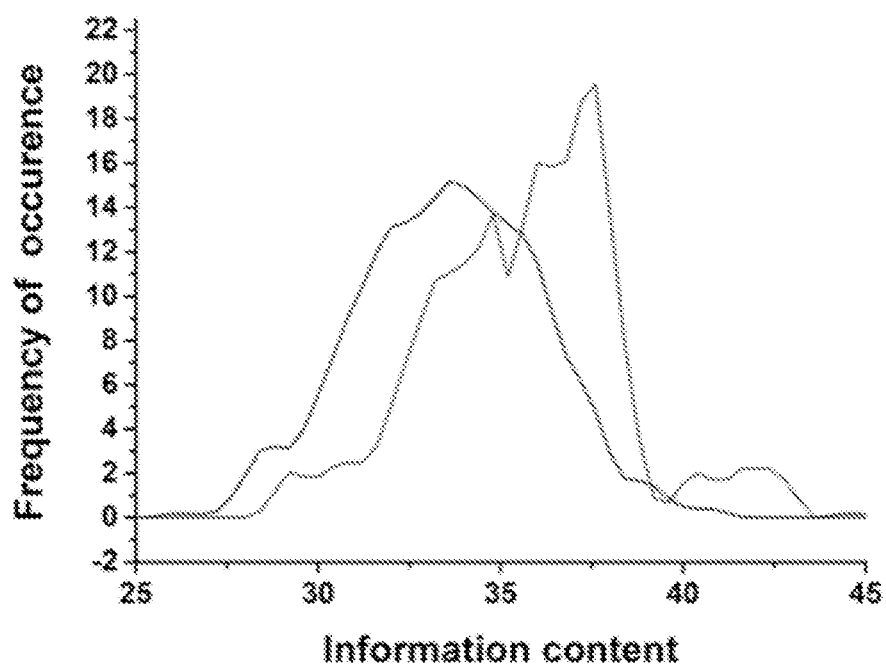
FIG. 2 shows a graphical representation of the output from RELIC/INFO for the results of FIG. 1. The curve with the left-most peak is the INFO-generated normalized information distribution of randomly chosen peptides derived from the Ph.D.-12 library. The curve with the right-most peak is the information distribution of affinity-selected peptides against angiogenin. A clear shift to higher information content is observed from biopanning The shift indicates the biopanning was performed successfully based on the affinity to angiogenin rather than the growth characteristics of the phage.

In order to identify the angiogenin-binding peptides, the phage biopanning was carried out following a standard protocol (FIG. 1). We chose the Ph.D.-12 phage library instead of other commonly used phagemid libraries since the peptides in the Ph.D.-12 phage library are fully displayed on all five copies of pIII proteins, while the peptides in the phagemid libraries are only partially displayed on pIII proteins (e.g. pSKAN Phagemid Display System, MoBiTec). After four rounds of affinity-selection was completed, the titers of the selected phages increased from 4.73×10$^4$ pfu/mL in the second round to 1.98×10$^6$ pfu/mL in the third round, and to 2.44×10$^6$ pfu/mL in the fourth round, indicating that the biopanning was performed successfully. In the fourth rounds of selection, 57 plaques from each round were sent for DNA sequencing. The sequencing results showed the peptide WPYWNHHSHNNV (SEQ ID NO:1, termed WV) had 11 repeats, FHHPSIHDRHRH (SEQ ID NO:2, termed FH) had 4 repeats, and each of the other 42 sequences only had 1 repeat. To ulteriorly assay whether the high frequent peptides observed from the biopanning is based on the affinity or the growth properties, the REceptor LIgand Contacts (RELIC/INFO) program was used to assay the affinity-selected 57 peptides and the parent Ph.D.-12 library. The distribution of information content of the affinity-selected subset and the parent library shows that a clear shift occurs between them (FIG. 2). This result indicated that the identified peptides containing the high frequency is based on the affinity rather than growth characteristics. Therefore, the two peptides with 4 or more repeats (FH and WV) had higher angiogenin-binding affinity.

Binding-Affinity of the High Frequency Phages

Figure 3:
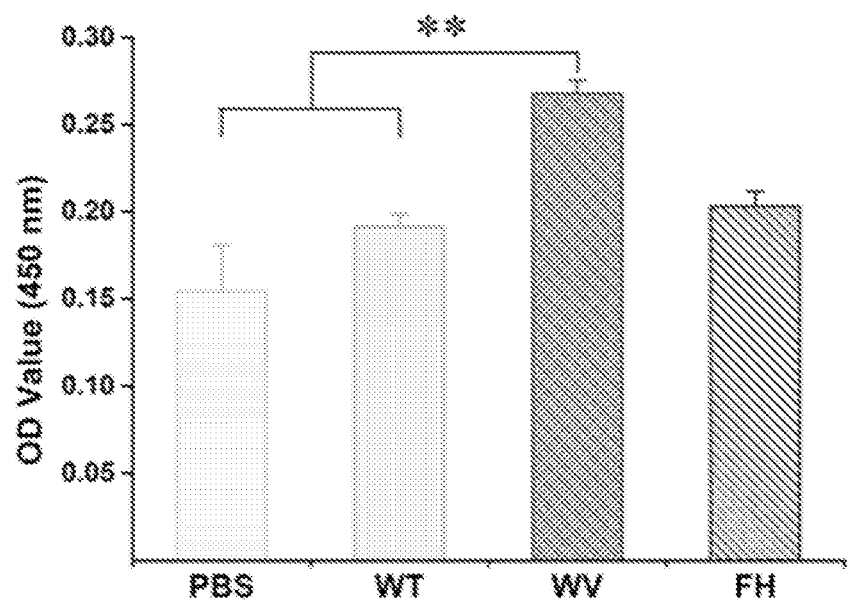
FIG. 3 shows results from an ELISA assay showing the interaction between angiogenin and the phages displaying peptides with a high occurrence frequency phage. For each phage type, 1×10$^9$ pfu of phages were incubated with coated angiogenin. The results show that the bearing phage bearing WV peptide (SEQ ID NO:1) has the highest binding affinity for angiogenin. Each value represents the mean of four repeated independent experiment±standard deviation (SD). The statistical test method is t-test, and the WV peptide-bearing phage has a statistically significant increase compared with the wild type phage and blank control (**$p<0.01$).
Figure 4:
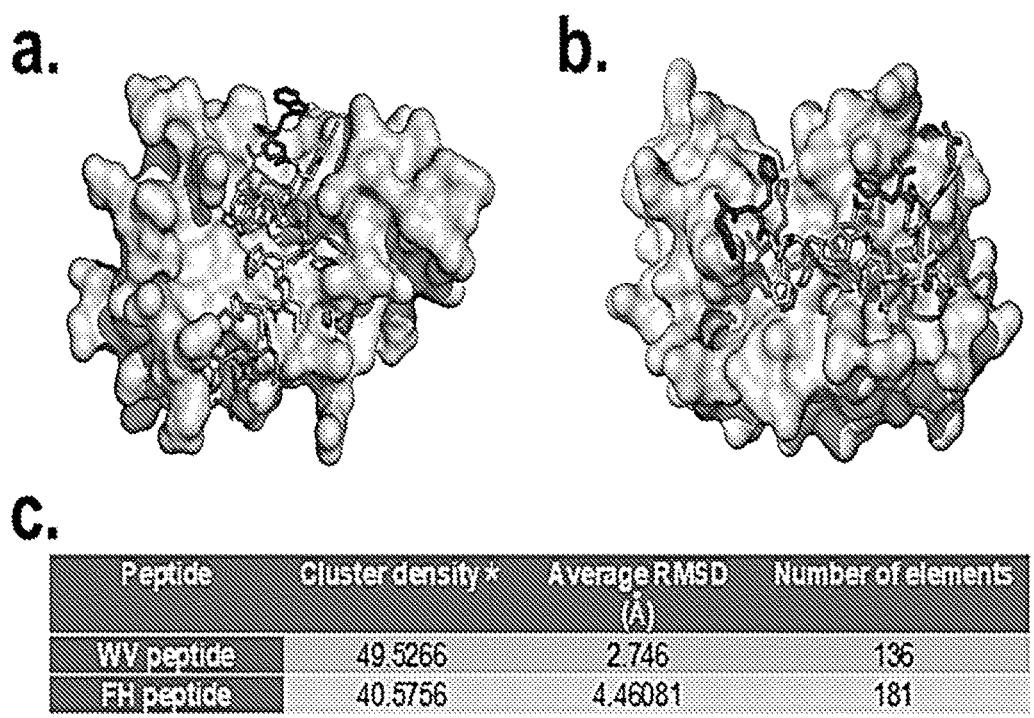
FIG. 4 shows Molecular simulation (MD) of the binding between the identified peptides (rainbow) and the angiogenin protein (gray, PDB ID: 5M9V) (a) CABS-docking modeling of WV peptide bound in the angiogenin; (b) CABS-docking modeling of FH peptide bound in the angiogenin; (c) the detailed information of the peptide clusters binding with the angiogenin. *Cluster density is the N/avg-RMSD, where the N is number of elements in cluster and the avg-RMSD is average RMSD between the cluster elements.
Figure 5:
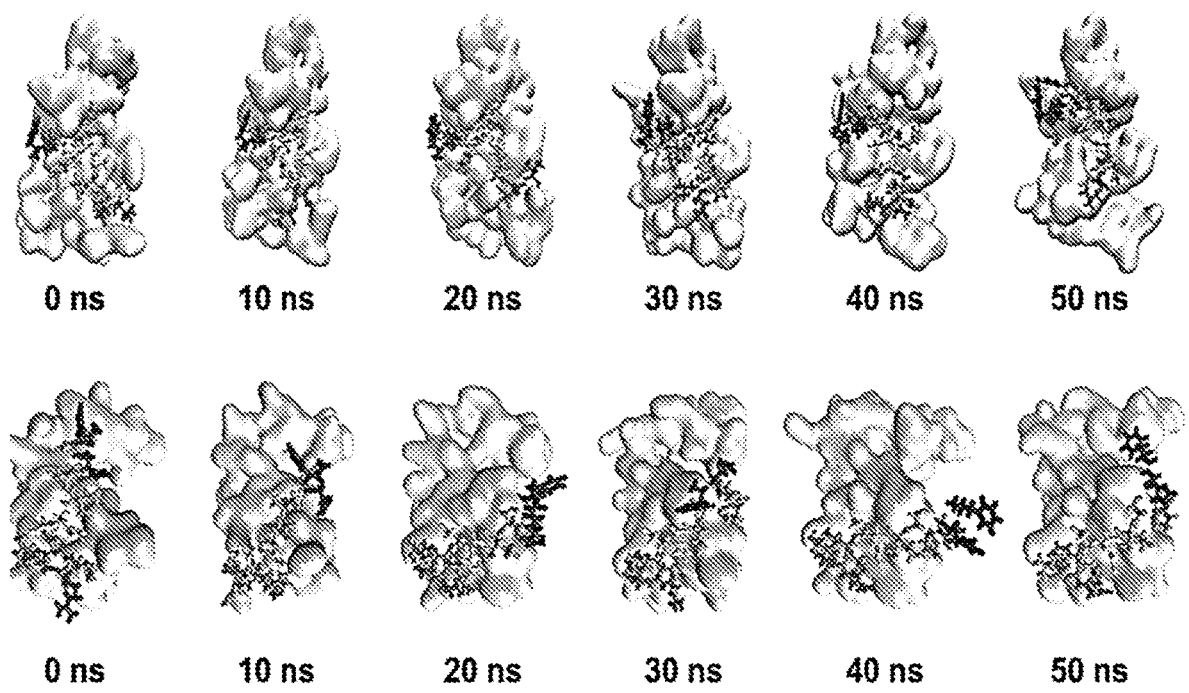
FIG. 5 shows MD snapshots of the angiogenin interacting with WV/FH peptides. The top/bottom rows represent the MD simulation of the WV/FH peptides bind with the angiogenin, respectively. The MD simulation results were visualized using VMD with 10 ns interval. It showed that the bound structure of WV peptide and the angiogenin was stable for 50 ns, but that of FH peptide and the angiogenin was changed more frequently and vigorously.

To test the binding-affinity of the two high frequency peptides (WV and FH) against angiogenin, a phage ELISA was performed. The ELISA result (FIG. 3) shows the OD value of the WV peptide-bearing phage (0.26775±0.00754) is significantly higher (p<0.01) than that of WT phage (0.19125±0.00741). Whereas, the FH peptide also has a high frequency in the DNA sequencing, but the OD value of the FH peptide-bearing phage (0.203±0.00852) did not show significantly higher than the OD value of the WT phage. It indicated the WV peptide-bearing phage has the highest affinity toward the angiogenin comparing with the wild type phage and the FH peptide-bearing phage. To investigate the interactions of the angiogenin protein (PDB ID: 5M9V) with the WV and FH peptides, the online CABS-docking web server was used to predicate the docking site because of no 3D structures available for these 12 aa peptides. The best CABS-docking models of the WV (FIG. 4a) and the FH peptide (FIG. 4b) were chosen based upon the cluster density and the average RMSD (FIG. 4c). Thereafter, the two chosen models were used as the initial structures to perform the molecular dynamical (MD) simulation. A 50 ns of the MD simulation results demonstrated the WV peptide (FIG. 5, top row) could bind with the angiogenin more stability than the FH peptide (FIG. 5, bottom row). Only the WV peptide was used for the subsequent studies.

Global Characterization of the Angiogenin-Binding Peptides

Recent research demonstrated that angiogenin needs to bind the membrane receptor protein (FHL3, Four and a half LIM domains 3) of the endothelial cell and endocytose into cell to process its angiogenesis function. Therefore, we used the RELIC/MATCH program to align our affinity-selected peptides with FHL3 to identify potential angiogenin-binding domains. The RELIC/MATCH Program was used to align all the selected peptides with the whole amino acid sequences of FHL3 (NP_004459, 280 aa) from the first amino acid to the carboxyl terminal end, and give a modified BLOSUM62 score of the peptides aligned in each alignment. The align results show that the $_{238}$SFEDRHWHHN$_{247}$ (SEQ ID NO: 54) sequence of FHL3 has similar H×H×N, SF××R, and PY××H motifs as the WPYWNHHSHNNV peptide, evidencing that the WV peptides could capture the angiogenin and compete with FHL3 receptor protein.

Construction of Dual-Functional Phages

Figure 6:
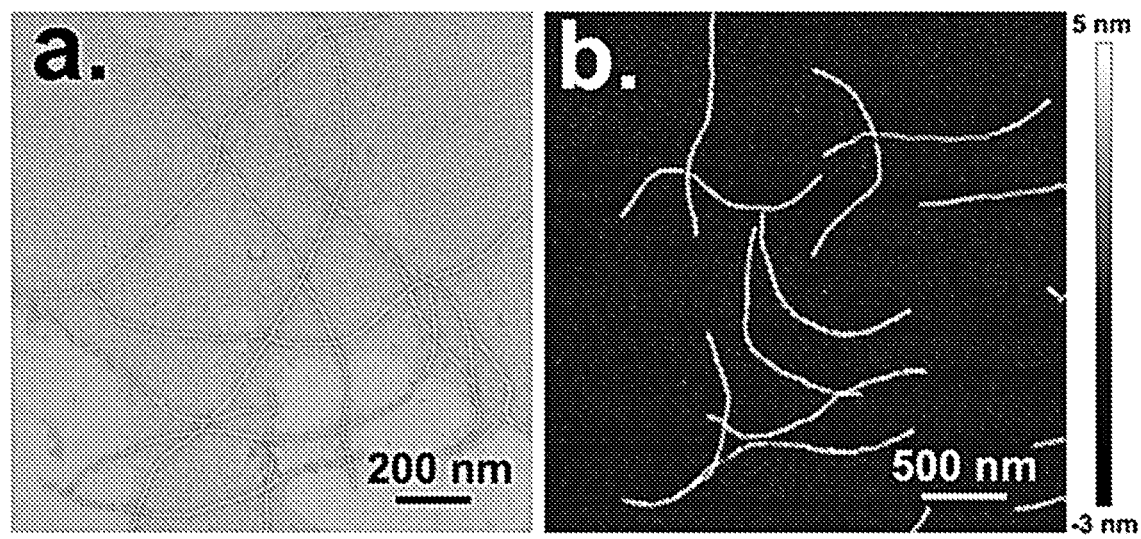
FIG. 6 shows TEM (a) and AFM (b) imaging showing that the fd388-AR-WV phage are filamentous.
Figure 7:
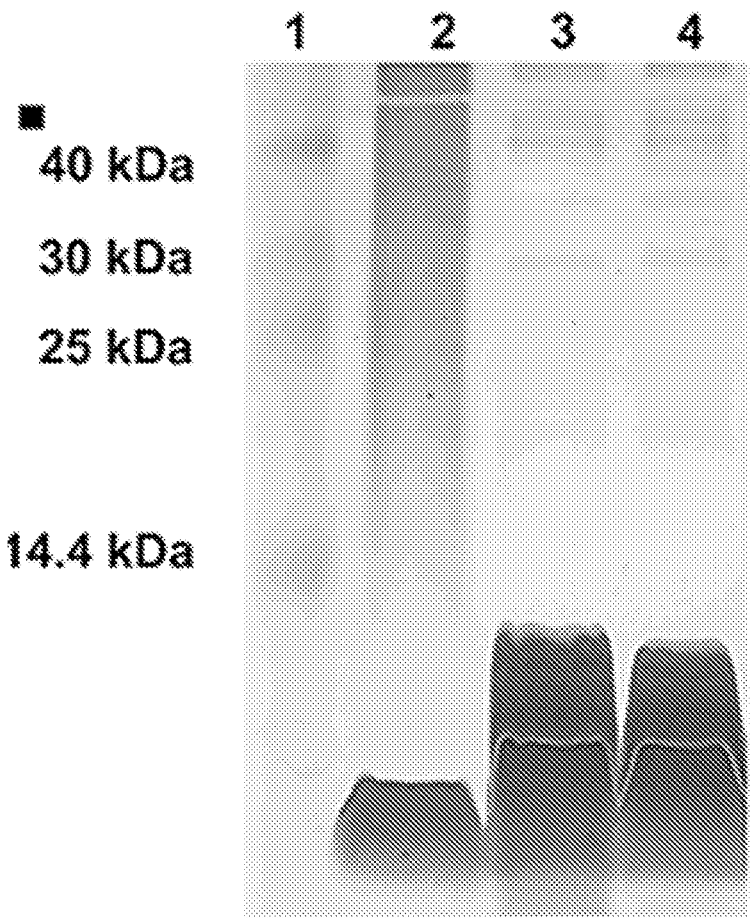
FIG. 7 shows SDS-PAGE and silver staining of the double-displayed phages (lane 1: Marker; lane 2: wild type phage; lane 3: fd388-AR-WV phage; lane 4: fd388-PW-WV phage). The SDS-PAGE result shows that the WV peptide has been fused to the pVIII of the fd388-AR-WV and fd388-PW-WV phage to form a recombinant protein.

In order to employ phage to inhibit the angiogenesis inner the breast tumor, the phage was modified using the home the MCF-7 breast tumor-homing peptide and angiogenin-binding peptide via genetics method. Firstly, the WV peptide was genetically displayed on the phage side wall (assemble from pVIII) to form fd388-WV phage. Then two tumor homing peptides (AREYGTRFSLIGGYR, "AR" and PKAFQYG-GRAVGGLW, "PW") with high homing ability to MCF-7 xenograft model were genetically displayed on one tip of the fd388-WV phage to form fd388-AR-WV and fd388-PW-WV, respectively. To insure the WV, AR and PW peptides were successfully displayed on the N terminal of the pIII and pVIII of the engineering phages, the recombinant plasmids (p-fd388-AR-WV and p-fd388-PW-WV) were sent to MCLAB for DNA sequencing firstly. Results showed the DNAs coding the three peptides were inserted into the correct site of the gene VIII and gene III of the double-display vector fd388. Then the corrected recombinant plasmids were transformed into the competent E. coli JM109 cell to amplify the fd388-AR-WV and fd388-PW-WV double-display phages. In the second, the TEM, AFM and SDS-PAGE assay were performed to validate the display, after the amplified phages were purified using the PEG/NaCl. The TEM and AFM images (FIG. 6a-b) show the fd388-AR-WV and fd388-PW-WV phage (1.3 μm in length and 7 nm in diameter) have been formed base on the accurate genetic engineering to correct the disrupted open reading frame (ORF) of gene III in the fd388 vector. Meanwhile, the silver staining image of SDS-PAGE shows two new bands occurred upon the pVIII bands of the fd388-AR-WV and fd388-PW-WV phage, but not in the wild type phage (FIG. 7). This indicates the peptide WV was correctly displayed on the pVIII coat protein of fd388-AR-WV and fd388-PW-WV phage as a fusion protein. To validate whether the fd388-AR-WV phage would maintain the ANG-binding affinity of the WV peptide, dot-blot hybridization was carried out. Results of the dot-blot hybridization of the phage and the angiogenin showed the fd388-AR-WV phage had strong binding to angiogenin, while the control wild type phage and fd388-AR-RS phage (RS, a random sequence peptide, WHKNYNWSMSTA (SEQ ID NO: 55) fused on the pVIII) did not bind with angiogenin (data not shown).

Bio-Distribution of the Dual-Functional Phage in Breast Tumor Orthotopic Xenograft Nude Mouse After the successful construction of the double-display phage, we then conducted in vivo experiments to test the effectiveness of homing in breast cancer. Before the in vivo experiments, a blood compatibility test of the dual-functional phage was performed. The fd388-AR-WV phage was incubated with the blood cells for 6 h at 37° C. to process the hemolysis assay before the in vivo treatments. The results showed the fd388-AR-WV phage cause 3.976% hemolysis while the 0.9% saline cause 4.285% hemolysis after 6 h of exposure, which is below the hemolysis rate threshold value of 5% according to ISO 10993-4:2017, meaning the fd388-AR-WV phage and WT phage have a good compatibility in the blood circulation system and could be used in the in vivo treatments.

Figure 8:
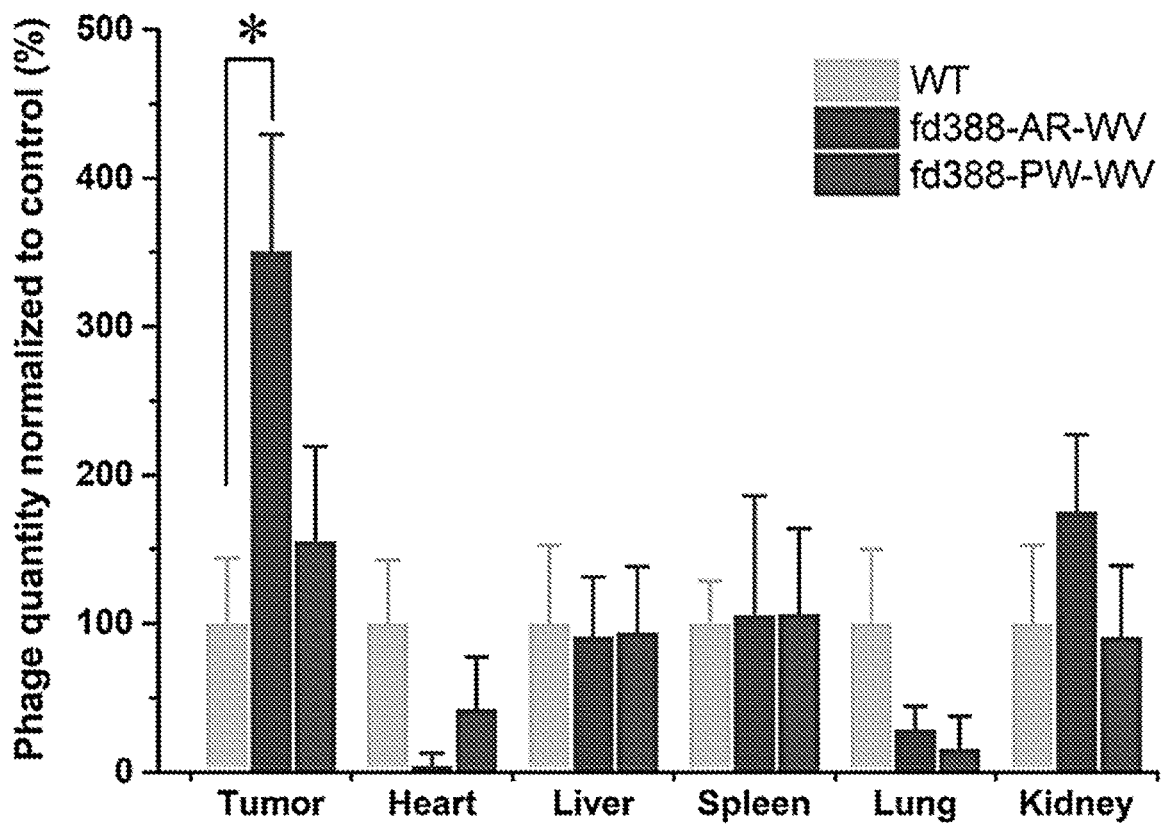
FIG. 8 shows the bio-distribution of double-displayed phages in the MCF-7 breast tumor orthotopic xenograft nude mice. The data is represented by the quantity of targeting phages (pfu per gram of tissue) normalized to the control (wild type phage) for each organ. $1\times10^9$ pfu of engineered phages (fd388-AR-WV or fd388-PW-WV) or wild type phages (blank control) are injected into the tail vein of the MCF-7 breast tumor bearing mice. After 4 h of blood circulation, the tumor and organs (heart, liver, spleen, lung and kidney) are excised and grinded. Then the grinded tissues are diluted 10-fold using sterile PBS buffer, and the quantity of the phages in the tissues is then determined by a titer assay. The data shows that the titer of the fd388-AR-WV phages accumulated in the tumor is significantly higher than that of the wild type phages. The value is mean of 5 independent repeats±SD. *$p<0.05$.

Afterwards, the orthotopic breast tumor-bearing nude mice animal model was used, as it could more similarly simulate the early-stage development of breast tumor (e.g., gene expression, histology, vascularity, metastatic biology) in human beings. The double-displayed fd388-AR-WV, fd388-PW-WV, and wild type phages were injected into the tail vein of the MCF-7 tumor orthotopic xenograft mice and circulated for 4 h, respectively. After the heart perfusion was completed, the tumor and main organs were harvested and grinded to release the phages. Then, the titering assay of these phages was performed to study their bio-distribution and targeting capability to the breast tumor. The titering results showed the amount of the fd388-AR-WV phages in the MCF-7 breast tumor was significantly higher (about 4 times) than the wild type phage group, demonstrating that this type of phage is able to recognize and enrich in the tumor of the orthotopic xenograft mice, because of the presence of the MCF-7 tumor-homing peptide (AR) displaying on the tip of phage particles (FIG. 8). However, the fd388-PW-WV phage did not show obvious higher enrichment in the tumor than the WT phage, suggesting that the AR peptide maintains a high affinity to the breast tumor after displaying on the filamentous phage than the PW peptide. Phages enriched in liver, spleen and kidney may be caused by the phages were needed to cleared by using the urinary and hepatobiliary organs of the reticuloendothelial system (RES).

Inhibition of Tumor Growth by Dual-Functional Phage

Figure 9:
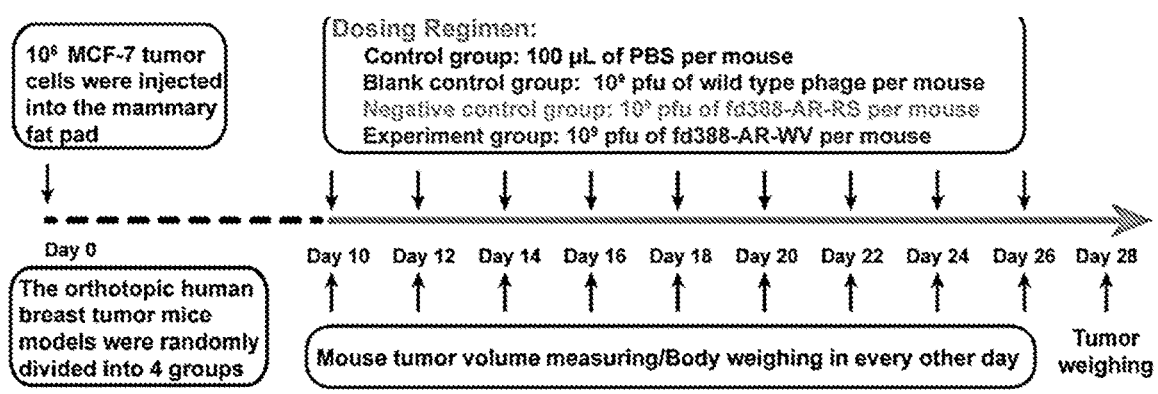
FIG. 9 shows a dosage regimen of the tumor growth inhibition (antitumor therapy) using the engineered dual-functional phages.
Figure 10:
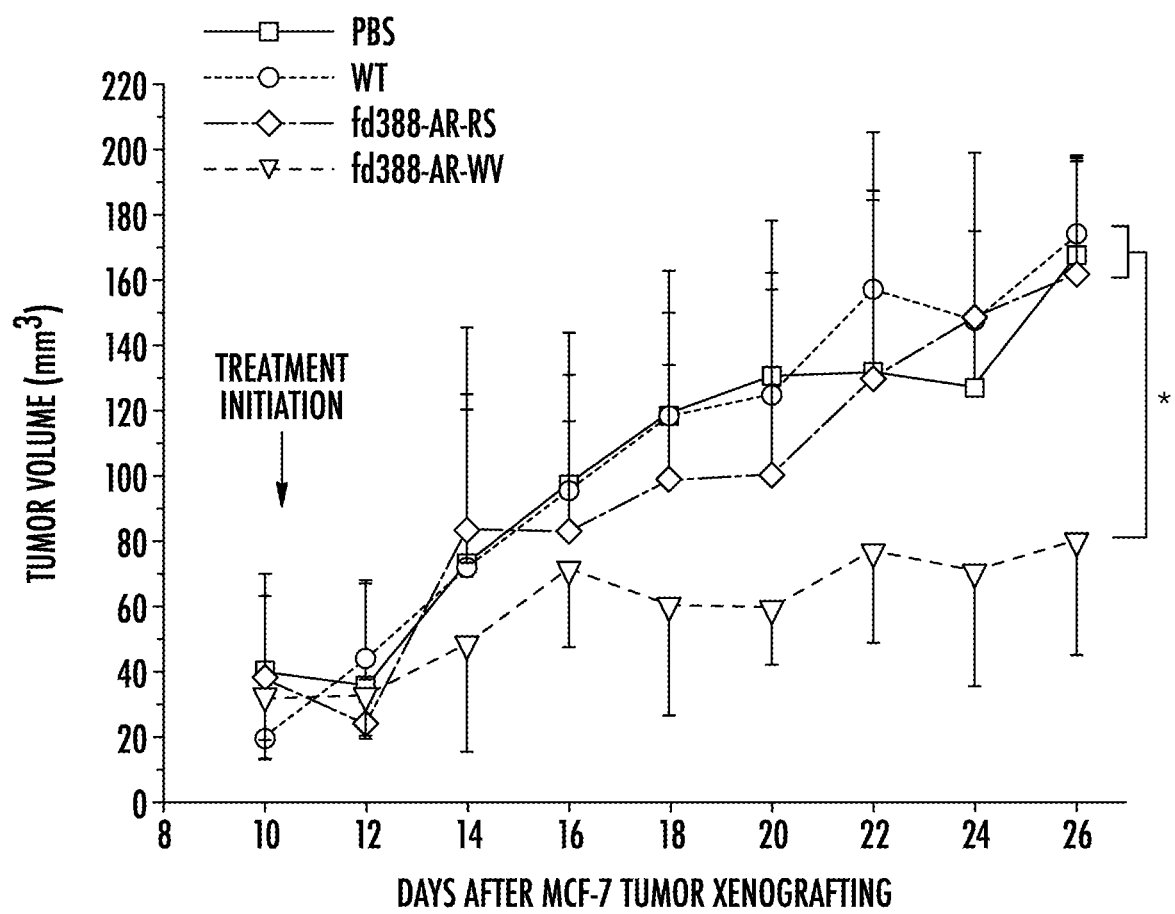
FIG. 10 shows tumor volumes in different treatment groups after treatment with the dual-functional phages. Tumors in the fd388-AR-WV group are significantly smaller than those in the other groups, and that volumes remain nearly unchanged after 16 days while the tumors in other groups continue to grow rapidly.
Figure 11:
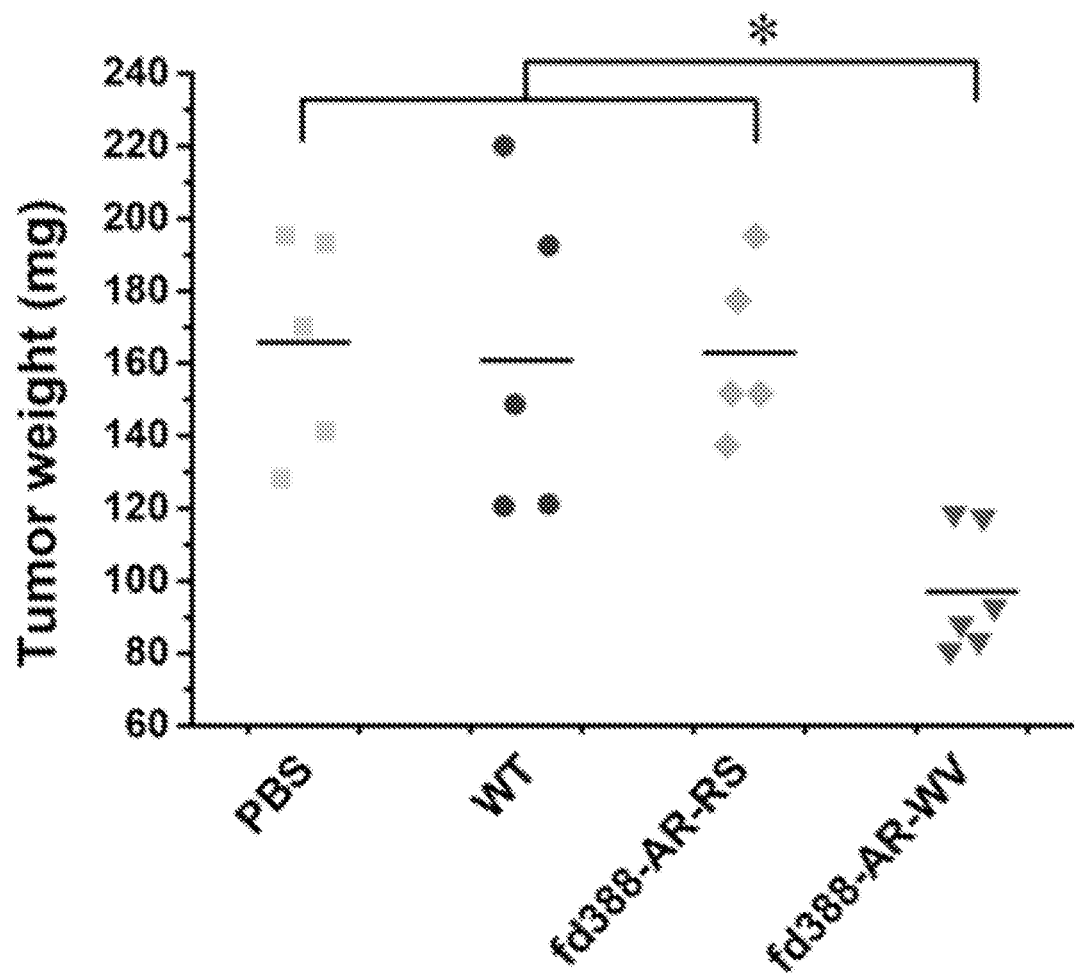
FIG. 11 shows tumor weights in the different treatment groups after 28 days, showing that with the tumor weight in the fd388-AR-WV group is significantly lower than the other groups.
Figure 13:
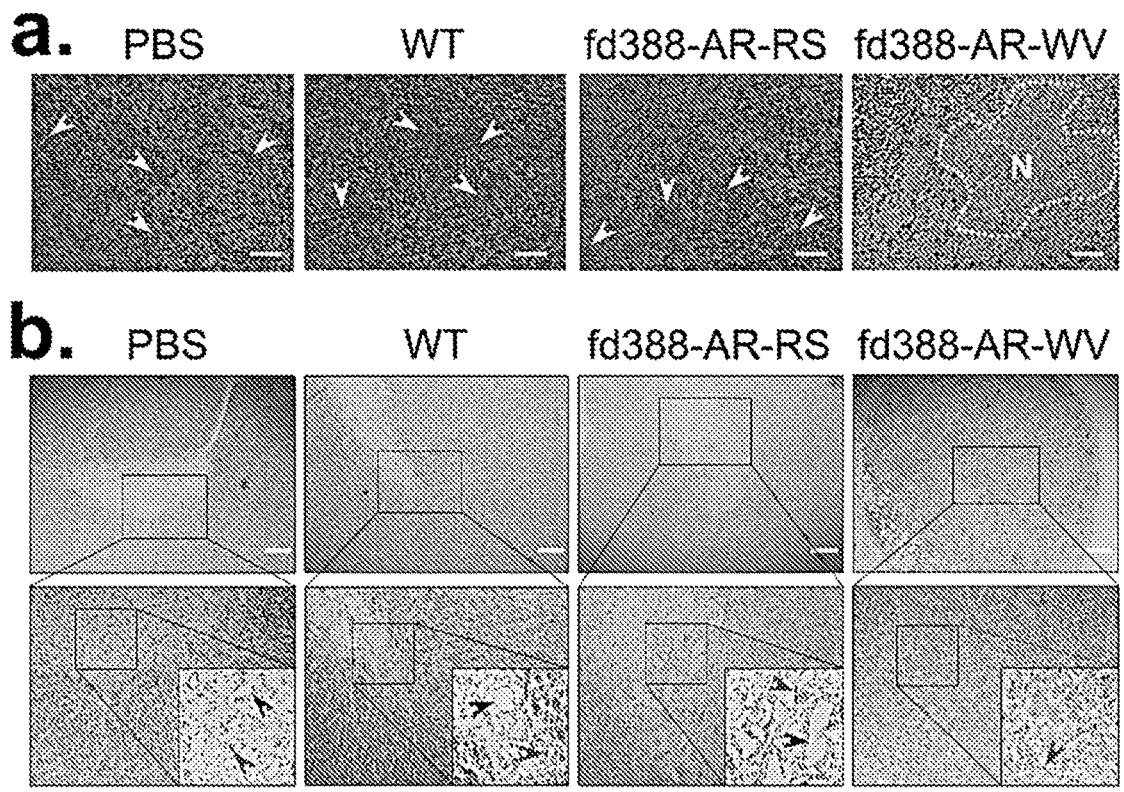
FIG. 13 shows results of histochemical and immunohistochemical assays of the tumors and intratumoral vessels from the treatment groups: (a) H&E staining images of the tumors show that necrosis occured in the tumors treated with fd388-AR-WV phage (in the area enclosed by the dotted line and denoted as "N", but is not observed in other groups. Meanwhile, no microvessels occur in the necrosis area in the fd388-AR-WV phage group microvessels, but they are observed in the other groups (white arrows indicate the blood vessels) Scale bars, 100 μm, (b) microscope images of the intratumoral microvessels on the $18^{th}$ day after treated with different phages show that almost no brown stained CD31-possitive cells clusters are found in the tumor treated with fd388-AR-WV phage, but many brown stained CD31-possitive cell clusters (represented by black arrows) and vessel lumens (pointed by red arrows) are found in the other groups. Scale bars, 200 μm.

In order to investigate evaluate the therapeutic effect of the dual-functional phage for breast cancer treatment, the MCF-7 orthotopic xenograft mice model was utilized. The fd388-AR-WV phage, PBS, WT, and the fd388-AR-RS phage as control group, was injected into the tail vein of the xenograft mice at a dose of $10^9$ pfu every other day from the $10^{th}$ day after the orthotopic xenotransplantation of the MCF-7 cancer cell, while several microvessels formed in the tumor when the diameter of the tumor lager than 2 mm$^3$ (FIG. 9). The tumor volume measurements showed that after the treatment with the fd388-AR-WV phage, the tumors grew significantly more slowly than those treated with PBS, WT phage or fd388-AR-RS phage (FIG. 10). The weight of the xenograft tumors on the $18^{th}$ day after treated with fd388-AR-WV phage was significantly smaller than PBS (58.47%), WT (60.31%) and fd388-AR-WV (59.53%) control group (FIG. 11). Importantly, the breast tumor treated with fd388-AR-WV phage remained unchanged at 75 mm$^3$ from the $16^{th}$ d. The H&E image of tumor tissue with treatment shows that some necrosis ("N") occurred in the tumor treated by fd388-AR-WV phage (FIG. 13a), but not in the control groups. And the H&E staining images still show no microvessels occurred around the necrosis area of the tumor with treatment of fd388-AR-WV, comparing with the control group (FIG. 13a). The results indicate that the fd388-AR-WV phage inhibits the tumor growth.

Figure 14:
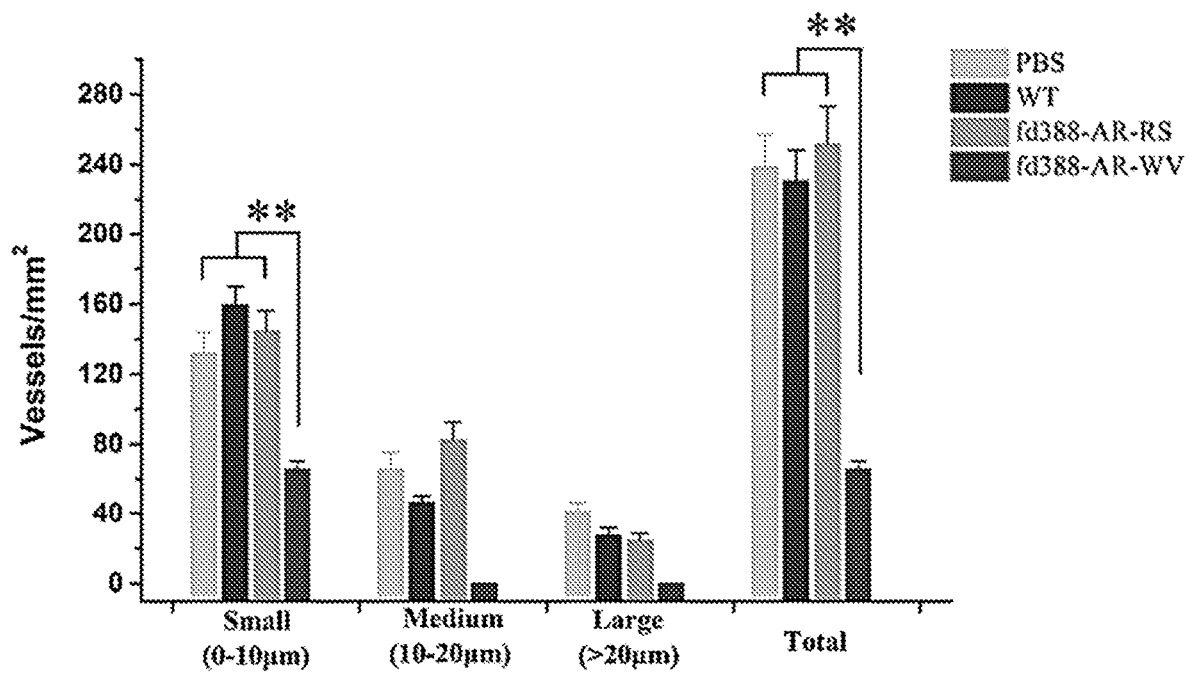
FIG. 14 shows a quantitative assay of microvessel density (MVD) of the tumors from the treated animals. Intratumoral MVD after treatment with fd388-AR-WV phage is significantly lower than that in the PBS, wild type, and fd388-AR-RS phage groups by factors of 72.41%, 71.42% and 73.83%, respectively. The value represents the mean of the density of the vessels in 3 random respective field per section±SD.**$p<0.01$. The fd388-AR-WV phage group does not present vessels with a medium or large diameter (larger than 10 μm, black arrows point), but only presents some small vessels (with a diameter smaller than 10 μm, red arrows point) with a density significantly lower than that of the other groups. However, for the other groups, vessels with low, medium and large diameters are all found.

Influence of Dual-Functional Phage on Tumor Vessel Formation and MCF-7 Proliferation To validate whether or not the dual-functional phages influenced new vessel formation to inhibit tumor growth, we assayed the microvascular of the tumor on $18^{th}$ day after treatment with phages. The tumor tissue after treatment was stained with anti-CD31 antibody to mark the CD31 (a molecular marker of endothelial cells). And the distinct CD31 positive vessel lumen and cell cluster was counted as the formed vessels. The immunhistochemical images show MVD (microvessel density) of the tumor treat with fd388-AR-WV decreased 72.41%, 71.42% and 73.83% than the PBS, WT and fd388-AR-RS phage (FIG. 13b, FIG. 14). The diameter of all the intratumoral vessels treated by fd388-AR-WV phage is less than 10 μm, but a half of vessels are larger than 10 μm in the control groups (treated with PBS, WT and fd388-AR-RS) (FIG. 13b, FIG. 14). These results indicated that the double-functional fd388-AR-WV phage inhibit angiogenesis within the tumor to suppress the tumor growth.

Systemic Toxicity and Cytotoxicity Assay of the Dual-Functional Phage

Figure 12:
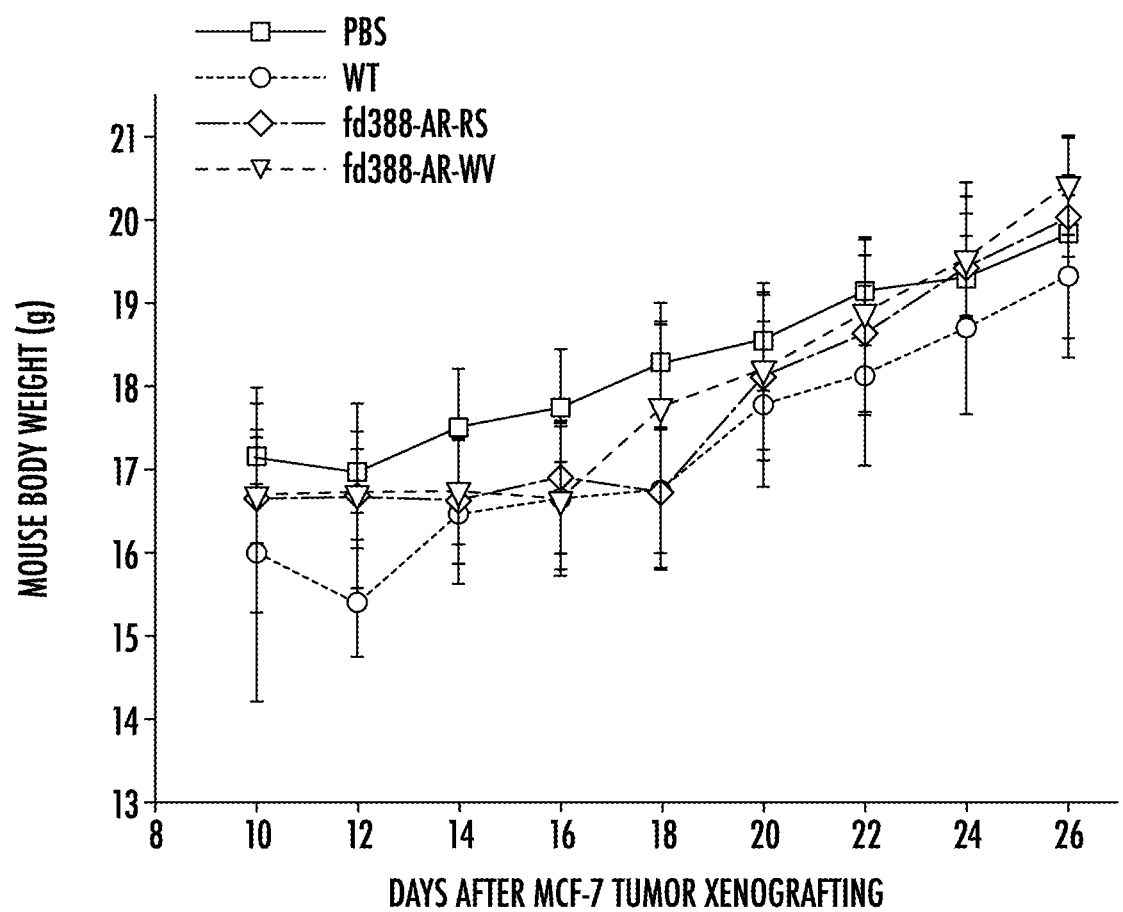
FIG. 12 shows body weight of the breast tumor xenograft mice with different treatments measured after every treatment, showing no significant difference in the body weight between different treatments. Each value represents the mean of repeated independent experiments±SD.*$p<0.05$.

To assess the systemic toxicity of the dual-functional phage, the mouse body weight monitoring, histology of the major organs and blood compatibility assay were processed. Overall health effects on the mice were monitored by weighing at every treatment time. The results show the weight of mice treated with PBS, WT, fd388-AR-RS and fd388-AR-WV increase at the same speed (FIG. 12). After treating with the phage, the main organs (heart, liver and kidney) sections were performed the H&E staining. H&E staining images showed no significant abnormalities, inflammation or disturbed areas occurred in all the major organs (heart, liver and kidney) of the mice treat with the fd388-AR-WV and the control group. It indicated that the fd388-AR-WV phage has a high compatibility with tumor bearing mice model.

To validate the cytotoxicity, MCF-10A cells, a non-tumorigenic human mammary epithelial cell line, was co-incubated fd388-AR-WV phage at 37° C. for 24 h, then stained with live/dead staining kit. Fluorescent images showed fd388-AR-WV phage do not induce the MCF-10A death comparing with the PBS (not shown). Meanwhile, the alamarBlue solution was used to measure the cell viability of the MCF-10A which have been treated with phage for 24 h. The result shows there is no different cell viability between the treatment of the PBS, WT, fd388-AR-RS and fd388-AR-WV phage.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicants reserve the right to amend, add to, or replace the claims indicated herein below in this or subsequent patent applications.

REFERENCES

Qu, X. W., Qiu, P. H., Zhu, Y., Yang, M. Y. & Mao, C. B. Guiding nanomaterials to tumors for breast cancer precision medicine: from tumor-targeting small-molecule discovery to targeted nanodrug delivery. *Npg Asia Mater.* 9, e452 (2017).

Frenkel, D. & Solomon, B. Filamentous phage as vector-mediated antibody delivery to the brain. *Proc. Natl. Acad. Sci. U.S.A.* 99, 5675-5679 (2002).

Wang, J., et al. Phage nanofibers induce vascularized osteogenesis in 3D printed bone scaffolds. *Adv. Mater.* 26, 4961-4966 (2014).

Staquicini, F. I., et al. Vascular ligand-receptor mapping by direct combinatorial selection in cancer patients. *Proc. Natl. Acad. Sci. U.S.A.* 108, 18637-18642 (2011).

Krag, D. N., et al. Selection of tumor-binding ligands in cancer patients with phage display libraries. *Cancer Res.* 66, 7724-7733 (2006).

Wang, Y., et al. Ultrasensitive rapid detection of human serum antibody biomarkers by biomarker-capturing viral nanofibers. *ACS Nano* 9, 4475-4483 (2015).

Yang, M., Sunderland, K. & Mao, C. Virus-Derived Peptides for Clinical Applications. *Chem. Rev.* 117, 10377-10402 (2017).

Yang, M., et al. Evolutionary selection of personalized melanoma cell/tissue dual-homing peptides for guiding bio-nanofibers to malignant tumors. *Chem. Commun.* 54, 1631-1634 (2018).

Yoshioka, N., Wang, L., Kishimoto, K., Tsuji, T. & Hu, G.-f. A therapeutic target for prostate cancer based on angiogenin-stimulated angiogenesis and cancer cell proliferation. *Proc. Natl. Acad. Sci. U.S.A.* 103, 14519-14524 (2006).

Ghosh, D., et al. M13-templated magnetic nanoparticles for targeted in vivo imaging of prostate cancer. *Nat. Nanotechnol.* 7, 677-682 (2012).

Gho, Y. S., Lee, J. E., Oh, K. S., Bae, D. G. & Chae, C. B. Development of antiangiogenin peptide using a phage-displayed peptide library. *Cancer Res.* 57, 3733-3740 (1997).

What is claimed is:

1. A peptide composition, comprising:
a peptide linked to a carrier, the peptide comprising an amino acid sequence selected from the group consisting of WPYWNHHSHNNV (SEQ ID NO:1) and FHHPSIHDRHRH (SEQ ID NO:2), and variant sequences thereof, wherein the variant sequence has at least 83% identity with one of SEQ ID NO:1-2.

2. The peptide composition of claim 1, further comprising a tumor-homing peptide linked to the carrier.

3. The peptide composition of claim 1, wherein the carrier is selected from nanoparticles, liposomes, polymeric drug scaffolds and polymeric micelles.

4. The peptide composition of claim 3, wherein the nanoparticle is a bacteriophage, bacteriophage fragment, virus, virus fragment, nano-cage, nano-rod, or nano-dendrite.

5. The peptide composition of claim 4, wherein the bacteriophage or bacteriophage fragment is an M13, fl, or fd phage, or a fragment thereof.

6. The peptide composition of claim 1, wherein the variant sequence has at least 91% identity to one of SEQ ID NO:1-2.

7. The peptide composition of claim 1, wherein the peptide is directly linked by a covalent bond to the carrier.

8. The peptide composition of claim 1, wherein the peptide is linked to the carrier via a linker sequence.

9. The peptide composition of claim 1, wherein the peptide comprises the amino acid sequence SEQ ID NO:1, or the variant sequence thereof having at least 83% identity thereto.

10. The peptide composition of claim 1, wherein the peptide comprises the amino acid sequence SEQ ID NO:2, or the variant sequence thereof having at least 83% identity thereto.

11. A method of inhibiting angiogenesis in a subject in a subject in need of such therapy, comprising: administering to the subject an effective amount of a peptide composition comprising a peptide linked to a carrier, the peptide comprising an amino acid sequence selected from the group consisting of WPYWNHHSHNNV (SEQ ID NO:1) and FHHPSIHDRHRH (SEQ ID NO:2), and variant sequences thereof, wherein the variant sequence has at least 83% identity with one of SEQ ID NO:1-2.

12. The method of claim 11, wherein the peptide composition further comprises a tumor-homing peptide linked to the carrier.

13. The method of claim 11, wherein the carrier is selected from nanoparticles, liposomes, polymeric drug scaffolds and polymeric micelles.

14. The method of claim 13, wherein the nanoparticle is a bacteriophage, bacteriophage fragment, virus, virus fragment, nano-cage, nano-rod, or nano-dendrite.

15. The method of claim 14, wherein the bacteriophage or bacteriophage fragment is an M13, fl, or fd phage, or a fragment thereof.

16. The method of claim 11, wherein the variant sequence has at least 91% identity to one of SEQ ID NO:1-2.

17. The method of claim 11, wherein the peptide is directly linked by a covalent bond to the carrier.

18. The method of claim 11, wherein the peptide is linked to the carrier via a linker sequence.

19. The method of claim 11, wherein the peptide of the peptide composition comprises the amino acid sequence SEQ ID NO:1, or the variant sequence thereof having at least 83% identity thereto.

20. The method of claim 11, wherein the peptide of the peptide composition comprises the amino acid sequence SEQ ID NO:2, or the variant sequence thereof having at least 83% identity thereto.

* * * * *

SEQUENCE LISTING

```
<160> NUMBER OF SEQ ID NOS: 55

<210> SEQ ID NO 1
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 1

Trp Pro Tyr Trp Asn His His Ser His Asn Asn Val
1               5                   10
```

```
<210> SEQ ID NO 2
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 2

Phe His His Pro Ser Ile His Asp Arg His Arg His
1               5                   10

<210> SEQ ID NO 3
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 3

Trp His Ser Pro Trp Arg Ser Trp Glu Val Arg Ser
1               5                   10

<210> SEQ ID NO 4
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 4

His Tyr Asn Lys Leu His Lys Pro Arg Ile Leu Tyr
1               5                   10

<210> SEQ ID NO 5
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 5

Gly His Ser Trp His Phe His Gly Arg Ser Pro His
1               5                   10

<210> SEQ ID NO 6
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 6

His Trp Thr Pro His Asn His Trp Arg Leu Ser Arg
1               5                   10
```

```
<210> SEQ ID NO 7
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 7

Phe Pro Asp His Phe Phe Trp Arg Leu His Arg Ser
1               5                   10

<210> SEQ ID NO 8
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 8

Glu His Trp Arg Trp Pro Trp Gln Asn Leu Trp Arg
1               5                   10

<210> SEQ ID NO 9
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 9

Trp Pro Asn His His His His Pro Arg Ala His Thr
1               5                   10

<210> SEQ ID NO 10
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 10

Val Asp Ala Ser His Arg Leu His Trp Arg Leu Lys
1               5                   10

<210> SEQ ID NO 11
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 11

Gly Tyr Ser His Lys His Phe Phe Thr Ser Lys Arg
1               5                   10
```

```
<210> SEQ ID NO 12
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 12

Trp Pro Arg Ser Ser His His Trp Tyr Gln His Thr
1               5                   10

<210> SEQ ID NO 13
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 13

Trp Pro Tyr His Arg Ser His Ala His Pro His Pro
1               5                   10

<210> SEQ ID NO 14
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 14

Ser Thr Gly His Trp His Arg Ser His Phe His Phe
1               5                   10

<210> SEQ ID NO 15
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 15

His Pro Met His Met Leu His Lys Arg Gln His Gly
1               5                   10

<210> SEQ ID NO 16
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 16

His Leu Phe Thr Arg His Pro His Tyr Gly Phe Gln
```

```
1               5                   10
```

<210> SEQ ID NO 17
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 17

```
His Phe Phe Asn Pro His Lys Ala Leu His Ser Lys
1               5                   10
```

<210> SEQ ID NO 18
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 18

```
Phe His Lys Thr Gly Asn Leu Ile Asn Pro Arg Trp
1               5                   10
```

<210> SEQ ID NO 19
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 19

```
Asp Met Ile Leu Ala His Thr Ser Gly Ser Ile Phe
1               5                   10
```

<210> SEQ ID NO 20
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 20

```
Gly Ala Asn Asp Gly Val Ser Leu Trp Arg Asn Val
1               5                   10
```

<210> SEQ ID NO 21
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 21

Trp His Lys Thr Pro Leu Tyr Thr Val Lys Gly Pro
1               5                   10

<210> SEQ ID NO 22
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 22

Phe Asn Pro Pro Arg Ala Thr Trp Leu Gly Thr Tyr
1               5                   10

<210> SEQ ID NO 23
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 23

Gly Pro Trp Lys Gln His Lys His Trp Leu Tyr Ala
1               5                   10

<210> SEQ ID NO 24
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 24

Trp Pro His Asn His Trp Arg Asn Gln Ala Pro Ser
1               5                   10

<210> SEQ ID NO 25
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 25

Trp Ile Pro Arg His Trp His Glu His Leu Val Thr
1               5                   10

<210> SEQ ID NO 26
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library
<220> FEATURE:
<221> NAME/KEY: misc_feature

```
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 26

His Ser Trp Xaa Ser Trp Xaa Leu Gln Asn Arg Xaa
1               5                   10

<210> SEQ ID NO 27
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 27

Gln Val Asn Gly Leu Gly Glu Arg Ser Gln Gln Met
1               5                   10

<210> SEQ ID NO 28
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 28

Gly Trp Trp His Pro Lys Ala Pro Pro Pro Lys Pro
1               5                   10

<210> SEQ ID NO 29
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 29

Leu Thr Gly Gly His Leu His Gly Ser Val Arg His
1               5                   10

<210> SEQ ID NO 30
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 30

Leu Glu Gln Pro Gly His Ser Val Leu Ser His Arg
1               5                   10
```

```
<210> SEQ ID NO 31
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 31

Trp Ser Trp His Gly Leu Asp Trp Arg Trp Arg Ser
1               5                   10

<210> SEQ ID NO 32
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 32

His Met Thr Ala Trp His Gln His Arg Ser Asn Thr
1               5                   10

<210> SEQ ID NO 33
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 33

Gly Pro Phe Lys Met His Arg Trp Leu Pro His Thr
1               5                   10

<210> SEQ ID NO 34
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 34

Asn His Phe Thr Leu Thr Arg His Thr His Tyr Lys
1               5                   10

<210> SEQ ID NO 35
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 35

Gly Pro His Tyr Tyr His Pro Trp Lys His Arg Ala
```

<210> SEQ ID NO 36
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 36

Trp Pro Thr His Ser His Arg Gly Tyr Phe Phe Val
1               5                   10

<210> SEQ ID NO 37
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 37

Ser His Trp Ser Ser Tyr Phe His Pro Arg Gly Asn
1               5                   10

<210> SEQ ID NO 38
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 38

Gly Phe Phe Asp Lys His Arg Ser Trp His Ile Thr
1               5                   10

<210> SEQ ID NO 39
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 39

His Ile Lys Trp Asn Ile Ser Asn Ser Ile Ser Thr
1               5                   10

<210> SEQ ID NO 40
<211> LENGTH: 12
<212> TYPE: PRT
<213> ORGANISM: Artificial sequence
<220> FEATURE:
<223> OTHER INFORMATION: Completely synthesized in the lab - Ph.D.-12
      Phage Display Peptide Library
<220> FEATURE:
<221> NAME/KEY: misc_feature
<222> LOCATION: (6)..(6)
<223> OTHER INFORMATION: Xaa can be any naturally occurring amino acid
<220> FEATURE:

```
<221> NAME/KEY: misc_feature
<222> LOCATION: (11)..(12)
<223> OTHER INFORMATION: Xaa can be any naturally occurring amino acid

<400> SEQUENCE: 40

Trp Asp Val His Ser Xaa Leu Gly His Arg Xaa Xaa
1               5                   10

<210> SEQ ID NO 41
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 41

His His Phe Ser Lys Leu Pro Leu Lys His Ser His
1               5                   10

<210> SEQ ID NO 42
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 42

Arg Asp Tyr His Pro Arg Asp His Thr Ala Thr Trp
1               5                   10

<210> SEQ ID NO 43
<211> LENGTH: 12
<212> TYPE: PRT
<213> ORGANISM: Artificial sequence
<220> FEATURE:
<221> NAME/KEY: PEPTIDE
<222> LOCATION: (1)..(12)
<223> OTHER INFORMATION: Completely synthesized in the lab - Ph.D.-12
      Phage Display Peptide Library

<400> SEQUENCE: 43

Trp His Arg Asp Phe Phe Pro Gln Ser Phe Arg Ser
1               5                   10

<210> SEQ ID NO 44
<211> LENGTH: 12
<212> TYPE: PRT
<213> ORGANISM: Artificial sequence
<220> FEATURE:
<223> OTHER INFORMATION: Completely synthesized in the lab - Ph.D.-12
      Phage Display Peptide Library
<220> FEATURE:
<221> NAME/KEY: misc_feature
<222> LOCATION: (12)..(12)
<223> OTHER INFORMATION: Xaa can be any naturally occurring amino acid

<400> SEQUENCE: 44

His Gly Ser Phe His Trp Arg Thr His Gly Leu Xaa
1               5                   10

<210> SEQ ID NO 45
<211> LENGTH: 15
<212> TYPE: PRT
```

```
<213> ORGANISM: Artificial sequence
<220> FEATURE:
<221> NAME/KEY: PEPTIDE
<222> LOCATION: (1)..(15)
<223> OTHER INFORMATION: Completely synthesized in the lab - phage
      library having GenBank Accession No. AF246445

<400> SEQUENCE: 45

Ala Arg Glu Tyr Gly Thr Arg Phe Ser Leu Ile Gly Gly Tyr Arg
1               5                   10                  15

<210> SEQ ID NO 46
<211> LENGTH: 15
<212> TYPE: PRT
<213> ORGANISM: Artificial sequence
<220> FEATURE:
<221> NAME/KEY: PEPTIDE
<222> LOCATION: (1)..(15)
<223> OTHER INFORMATION: Completely synthesized in the lab - phage
      library having GenBank Accession No. AF246445

<400> SEQUENCE: 46

Pro Lys Ala Phe Gln Tyr Gly Gly Arg Ala Val Gly Gly Leu Trp
1               5                   10                  15

<210> SEQ ID NO 47
<211> LENGTH: 15
<212> TYPE: PRT
<213> ORGANISM: Artificial sequence
<220> FEATURE:
<221> NAME/KEY: PEPTIDE
<222> LOCATION: (1)..(15)
<223> OTHER INFORMATION: Completely synthesized in the lab - phage
      library having GenBank Accession No. AF246445

<400> SEQUENCE: 47

Pro Val Arg Tyr Gly Phe Ser Gly Pro Arg Leu Ala Glu Leu Trp
1               5                   10                  15

<210> SEQ ID NO 48
<211> LENGTH: 15
<212> TYPE: PRT
<213> ORGANISM: Artificial sequence
<220> FEATURE:
<221> NAME/KEY: PEPTIDE
<222> LOCATION: (1)..(15)
<223> OTHER INFORMATION: Completely synthesized in the lab - phage
      library having GenBank Accession No. AF246445

<400> SEQUENCE: 48

Arg Asn Val Pro Pro Ile Phe Lys Glu Val Tyr Trp Ile Ala Gln
1               5                   10                  15

<210> SEQ ID NO 49
<211> LENGTH: 15
<212> TYPE: PRT
<213> ORGANISM: Artificial sequence
<220> FEATURE:
<221> NAME/KEY: PEPTIDE
<222> LOCATION: (1)..(15)
<223> OTHER INFORMATION: Completely synthesized in the lab - phage
      library having GenBank Accession No. AF246445

<400> SEQUENCE: 49

Arg Thr Leu Ile Arg Met Gly Thr Gly Ala His Ala Phe Ala Val
1               5                   10                  15

<210> SEQ ID NO 50
<211> LENGTH: 50
```

<212> TYPE: PRT
<213> ORGANISM: Artificial Sequence
<220> FEATURE:
<223> OTHER INFORMATION: Completely synthesized in the lab.
<220> FEATURE:
<221> NAME/KEY: PEPTIDE
<222> LOCATION: (1)..(50)
<223> OTHER INFORMATION: Any grouping of "Gly Gly Gly Gly Ser" may be
      present

<400> SEQUENCE: 50

Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
            20                  25                  30

Gly Gly Gly Gly Ser Gly Gly Gly Gly Ser Gly Gly Gly Gly Ser
        35                  40                  45

Gly Gly Gly Gly Ser
     50

<210> SEQ ID NO 51
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 51
ccctcatagt tagcgtaacg                                               20

<210> SEQ ID NO 52
<211> LENGTH: 51
<212> TYPE: DNA
<213> ORGANISM: Artificial Sequence
<220> FEATURE:
<223> OTHER INFORMATION: Completely synthesized in the lab.

<400> SEQUENCE: 52
agctttgcct ggccttattg gaatcatcat tcgcataata atgtgggtgc a            51

<210> SEQ ID NO 53
<211> LENGTH: 43
<212> TYPE: DNA
<213> ORGANISM: Artificial Sequence
<220> FEATURE:
<223> OTHER INFORMATION: Completely synthesized in the lab.

<400> SEQUENCE: 53
cccacattat tatgcgaatg atgattccaa taaggccagg caa                    43

<210> SEQ ID NO 54
<211> LENGTH: 10
<212> TYPE: PRT
<213> ORGANISM: Artificial Sequence
<220> FEATURE:
<221> NAME/KEY: PEPTIDE
<222> LOCATION: (1)..(10)
<223> OTHER INFORMATION: Completely synthesized in the lab.

<400> SEQUENCE: 54

Ser Phe Glu Asp Arg His Trp His His Asn
1               5                   10

<210> SEQ ID NO 55
<211> LENGTH: 12
<212> TYPE: PRT

```
<213> ORGANISM: Artificial Sequence
<220> FEATURE:
<221> NAME/KEY: PEPTIDE
<222> LOCATION: (1)..(12)
<223> OTHER INFORMATION: Completely synthesized in the lab.

<400> SEQUENCE: 55

Trp His Lys Asn Tyr Asn Trp Ser Met Ser Thr Ala
1               5                   10
```